US007777014B2

(12) United States Patent
Cattaruzza et al.

(10) Patent No.: US 7,777,014 B2
(45) Date of Patent: Aug. 17, 2010

(54) FUNCTIONAL CORRECTION OF THE $^{-786}$C/T-VARIANCE OF THE HUMAN ENOS-GENE

(75) Inventors: Marco Cattaruzza, Göttingen (DE); Markus Hecker, Göttingen (DE)

(73) Assignee: Avontec GmbH, Gottingen (DE)

( * ) Notice: Subject to any disclaimer, the term of this patent is extended or adjusted under 35 U.S.C. 154(b) by 605 days.

(21) Appl. No.: 10/527,785

(22) PCT Filed: Sep. 12, 2003

(86) PCT No.: PCT/DE03/03028

§ 371 (c)(1),
(2), (4) Date: Oct. 3, 2005

(87) PCT Pub. No.: WO2004/027062

PCT Pub. Date: Apr. 1, 2004

(65) Prior Publication Data

US 2006/0122134 A1    Jun. 8, 2006

(30) Foreign Application Priority Data

Sep. 12, 2002    (DE) ............................... 102 42 319

(51) Int. Cl.
*C07H 21/04* (2006.01)
(52) U.S. Cl. .................................................... 536/23.1
(58) Field of Classification Search ........................ None
See application file for complete search history.

(56) References Cited

U.S. PATENT DOCUMENTS

2002/0132234 A1*    9/2002    Moskowitz .................... 435/6

FOREIGN PATENT DOCUMENTS

| WO | WO 9511687 A1 * | 5/1995 |
| WO | WO 99/65928 | 12/1999 |
| WO | WO 01/53537 | 7/2001 |

OTHER PUBLICATIONS

Nasreen et al. (2002) Arterioscler Thromb. Vasc. Biol. 22:605-610.*
Shimasaki et al. (1998) J. Am. Coll. Cardiol. 31:1506-1510.*
Jen et al. (2000) Stem Cells 18:307-319.*
Opalinska et al. (2002) Nature Reviews 1:503-514.*
Cattaruzza et al., 2004, Circ. Res. 95:841-847.*
Melchers et al., 2006, Arthritis & Rheumatism 54:3144-3151.*
Zhang et al. (1995) J. Biol. Chem. 270:15320-15326.*
Exhibits referred to by Applicant in Declaration under 37 CFR 1.132 submitted Apr. 13, 2007; 20-page fax from Fullbright & Jaworski.*
Melchers et al. (2006) Arthritis Rheum. 54:3144-3151.*
Wattanapitaykul et al. (2001) Trends Pharmacol. Sci. 22:361.*
Cattaruzza et al. (2004) Circ Res. 95: 841-847.*
Morishita et al. (1995) Proc. Natl. Acad. Sci. (1995) 92:5855-5859.*
Morishita et al. (1998) Circ. Res. 82:1023-1028.*
Tomita et al. (2003) Gene therapy for arthritis Curr Drug Targets. Nov. 2003;4(8):609-12.*
Ghivizzani et al. (2001) DDT 6:259-267.*
Morishita et al. (1997) Nature Medicine 3:894-899.*
Buchwald et al., "Decoy oligodeoxynucleotide against activator protein-1 reduces neointimal proliferation after coronary angioplasty in hypercholesterolemic minipigs," *J. Am. Coll. Cardio.*, 39(4):732-738, 2002.
Cattaruzza et al., "The $^{-786}$ variant of the human endothelial nitric oxide synthase gen promoter is a risk factor for coronary heart disease," *Pfluegers Archiv. Eur. J. Physiol.*, In Abstract P 12-6, 443:S255, 2002.
Daugherty and Rateri, "T lymphocytes in atherosclerosis: the yin-yang of th1 and th2 influence on lesion formation," *Circ. Res.*, 90:1039, 2002.
Dötsch et al., "Increase of endothelial nitric oxide synthase and endothelin-1 mRNA expression in human placenta during gestation," *Eur. J. Ob. Gyn. Reprod. Biol.*, 97:163-167, 2001.
Gimbrone et al., "Endothelial dysfunction, hemodynamic forces, and atherogenesis$^{a,}$" *Ann. N.Y. Acad. Sci.*, 920:230, 2000 (Abstract).
Lienenlüke et al., "CD154 stimulation of interleukin-12 synthesis in human endothelial cells," *Eur. J. Immunol.*, 30:2864, 2000.
Mann et al., "Ex-vivo gene therapy of human vascular bypass grafts with E2F decoy: the prevent single-centre, randomised, controlled trial," *Lancet*, 354: 1493, 1999.
Marsden et al., "Structure and chromosomal localization of the human constitutive endothelial nitric oxide synthase gene," *J. Biol. Chem.*, 268(23):17478-17488, 1993.
Miyamoto et al., "Replication protein A1 reduces transcription of the endothelial nitric oxide synthase gene containing a-786T→ C mutation associated with coronary spastic angina," *Hum. Mol. Gene.*, 9(18):2629-2637, 2000.
Moore et al., "Interleukin-10 and the interleukin-10 receptor," *Annu. Rev. Immunol.* 19:683-765, 2001.
Nakayama et al., "T$^{-786}$→ C mutation in the 5'-flanking region of the endothelial nitric oxide synthase gene is associated with coronary spasm," *Circulation*, 9:2684-2870, 1999.
Stojanovic et al., "STAT-1 decoy-oligodeoxynucleotide improvement of mucosal perfusion in a rat model of acute transplant rejection," *Chirugisches Forum*, 31:275-277, 2002.
Wagner et al., "Cytokine-inducible CD40 expresion in human endothelial cells in mediated by interferon regulatory factor-1," *Blood*, 99(2):520-525, 2002.
Wattanapitaykul et al., "Therapeutic implications of human endothelial nitric oxide synthase gene polymorphism," *Trends Pharmacol. Sci.*, 22:361, 2000, Abstract.
Cattaruzza et al., "Interleukin-10 Induction of Nitric-oxide Synthase Expression Attenuates CD40-mediated Interleukin-12 Synthesis in Human Endothelial Cells," *J. Biol. Chem.*, 278(30):37874-37880, 2003.
Asif et al., "Disinhibition of superoxide dismutase expression as a compensatory mechanism to overcome a genetically determined nitric oxide deficit in endothelial cells," Article Manuscript, In Press, 2008.
Cattaruzza et al., "Interleukin-10 Induction of Nitric-oxide Synthase Expression Attenuates CD40-mediated Interleukin-12 Synthesis in Human Endothelial Cells," *J. Biol. Chem.*, 278(30):37874-37880, 2003.

* cited by examiner

*Primary Examiner*—Louis Wollenberger
(74) *Attorney, Agent, or Firm*—Fulbright & Jaworski

(57) ABSTRACT

The present invention relates to decoy oligonucleotides with the nucleic acid sequence according to SEQ ID NO: 1 to 34 and their use as pharmaceutical agents. The present invention also discloses a method for diagnosis of the $^{-786}$C/T-variance in the eNOS-gene.

2 Claims, 8 Drawing Sheets

Fig. 1

Figure 2:
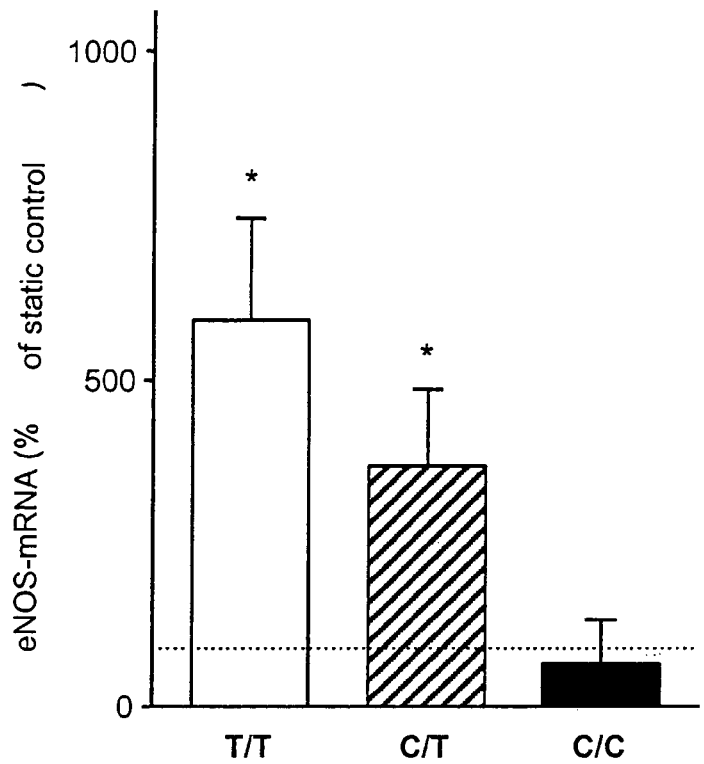
Figure 2:
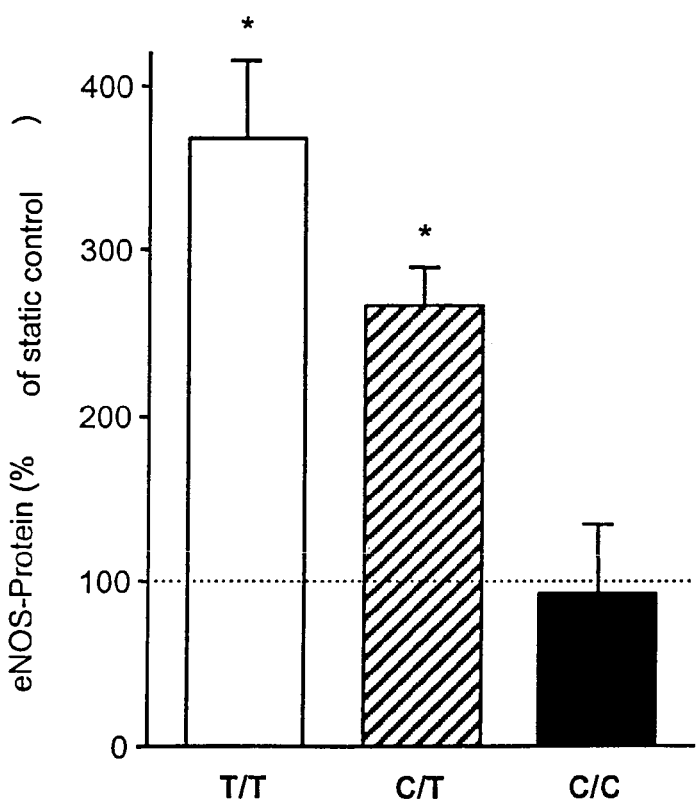

```
-871 CTGGTGTACCCCACCTGCATTCTGGGAACTGTAGTTTCCCTAGTCCCCCA
                       STAT      T
-821 TGCTCCCACCAGGGCATCAAGCTCTTCCCTGGCCGGCTGACCCTGCCTCA
                                       -786   c-Jun
```

A

B

SEQUENCE LISTING

<160> NUMBER OF SEQ ID NOS: 65

<210> SEQ ID NO 1
<211> LENGTH: 22
<212> TYPE: DNA
<213> ORGANISM: Artificial Sequence
<220> FEATURE:
<223> OTHER INFORMATION: Decoy-Oligonucleotide

<400> SEQUENCE: 1
agctcttccc tggccggctg ac                                              22

<210> SEQ ID NO 2
<211> LENGTH: 22

```
<212> TYPE: DNA
<213> ORGANISM: Artificial Sequence
<220> FEATURE:
<223> OTHER INFORMATION: Decoy-Oligonucleotide

<400> SEQUENCE: 2
gtcagccggc cagggaagag ct                                               22

<210> SEQ ID NO 3
<211> LENGTH: 22
<212> TYPE: DNA
<213> ORGANISM: Artificial Sequence
<220> FEATURE:
<223> OTHER INFORMATION: Decoy-Oligonucleotide

<400> SEQUENCE: 3
agctcttccc tggctggctg ac                                               22

<210> SEQ ID NO 4
<211> LENGTH: 22
<212> TYPE: DNA
<213> ORGANISM: Artificial Sequence
<220> FEATURE:
<223> OTHER INFORMATION: Decoy-Oligonucleotide

<400> SEQUENCE: 4
gtcagccagc cagggaagag ct                                               22

<210> SEQ ID NO 5
<211> LENGTH: 23
<212> TYPE: DNA
<213> ORGANISM: Artificial Sequence
<220> FEATURE:
<223> OTHER INFORMATION: Decoy-Oligonucleotide

<400> SEQUENCE: 5
cttccctggc cggctgaccc tgc                                              23

<210> SEQ ID NO 6
<211> LENGTH: 23
<212> TYPE: DNA
<213> ORGANISM: Artificial Sequence
<220> FEATURE:
<223> OTHER INFORMATION: Decoy-Oligonucleotide

<400> SEQUENCE: 6
gcagggtcag ccggccaggg aag                                              23

<210> SEQ ID NO 7
<211> LENGTH: 23
<212> TYPE: DNA
<213> ORGANISM: Artificial Sequence
<220> FEATURE:
<223> OTHER INFORMATION: Decoy-Oligonucleotide

<400> SEQUENCE: 7
cttccctggc tggctgaccc tgc                                              23

<210> SEQ ID NO 8
<211> LENGTH: 23
<212> TYPE: DNA
<213> ORGANISM: Artificial Sequence
<220> FEATURE:
<223> OTHER INFORMATION: Decoy-Oligonucleotide

<400> SEQUENCE: 8
```

```
gcagggtcag ccagccaggg aag                                           23

<210> SEQ ID NO 9
<211> LENGTH: 19
<212> TYPE: DNA
<213> ORGANISM: Artificial Sequence
<220> FEATURE:
<223> OTHER INFORMATION: Decoy-Oligonucleotide

<400> SEQUENCE: 9
gctcttccct ggccggctg                                                19

<210> SEQ ID NO 10
<211> LENGTH: 19
<212> TYPE: DNA
<213> ORGANISM: Artificial Sequence
<220> FEATURE:
<223> OTHER INFORMATION: Decoy-Oligonucleotide

<400> SEQUENCE: 10
cagccggcca gggaagagc                                                19

<210> SEQ ID NO 11
<211> LENGTH: 19
<212> TYPE: DNA
<213> ORGANISM: Artificial Sequence
<220> FEATURE:
<223> OTHER INFORMATION: Decoy-Oligonucleotide

<400> SEQUENCE: 11
caagctcttc cctggccgg                                                19

<210> SEQ ID NO 12
<211> LENGTH: 19
<212> TYPE: DNA
<213> ORGANISM: Artificial Sequence
<220> FEATURE:
<223> OTHER INFORMATION: Decoy-Oligonucleotide

<400> SEQUENCE: 12
ccggccaggg aagagcttg                                                19

<210> SEQ ID NO 13
<211> LENGTH: 19
<212> TYPE: DNA
<213> ORGANISM: Artificial Sequence
<220> FEATURE:
<223> OTHER INFORMATION: Decoy-Oligonucleotide

<400> SEQUENCE: 13
tcttccctgg ccggctgac                                                19

<210> SEQ ID NO 14
<211> LENGTH: 19
<212> TYPE: DNA
<213> ORGANISM: Artificial Sequence
<220> FEATURE:
<223> OTHER INFORMATION: Decoy-Oligonucleotide

<400> SEQUENCE: 14
gtcagccggc cagggaaga                                                19

<210> SEQ ID NO 15
<211> LENGTH: 19
<212> TYPE: DNA
<213> ORGANISM: Artificial Sequence
```

```
<220> FEATURE:
<223> OTHER INFORMATION: Decoy-Oligonucleotide

<400> SEQUENCE: 15
ctggccggct gaccctgcc                                                    19

<210> SEQ ID NO 16
<211> LENGTH: 19
<212> TYPE: DNA
<213> ORGANISM: Artificial Sequence
<220> FEATURE:
<223> OTHER INFORMATION: Decoy-Oligonucleotide

<400> SEQUENCE: 16
ggcagggtca gccggccag                                                    19

<210> SEQ ID NO 17
<211> LENGTH: 16
<212> TYPE: DNA
<213> ORGANISM: Artificial Sequence
<220> FEATURE:
<223> OTHER INFORMATION: Decoy-Oligonucleotide

<400> SEQUENCE: 17
tccctggccg gctgac                                                       16

<210> SEQ ID NO 18
<211> LENGTH: 16
<212> TYPE: DNA
<213> ORGANISM: Artificial Sequence
<220> FEATURE:
<223> OTHER INFORMATION: Decoy-Oligonucleotide

<400> SEQUENCE: 18
gtcagccggc caggga                                                       16

<210> SEQ ID NO 19
<211> LENGTH: 10
<212> TYPE: DNA
<213> ORGANISM: Artificial Sequence
<220> FEATURE:
<223> OTHER INFORMATION: Decoy-Oligonucleotide

<400> SEQUENCE: 19
ctggccggct                                                              10

<210> SEQ ID NO 20
<211> LENGTH: 10
<212> TYPE: DNA
<213> ORGANISM: Artificial Sequence
<220> FEATURE:
<223> OTHER INFORMATION: Decoy-Oligonucleotide

<400> SEQUENCE: 20
agccggccag                                                              10

<210> SEQ ID NO 21
<211> LENGTH: 10
<212> TYPE: DNA
<213> ORGANISM: Artificial Sequence
<220> FEATURE:
<223> OTHER INFORMATION: Decoy-Oligonucleotide

<400> SEQUENCE: 21
ctggctggct                                                              10
```

```
<210> SEQ ID NO 22
<211> LENGTH: 10
<212> TYPE: DNA
<213> ORGANISM: Artificial Sequence
<220> FEATURE:
<223> OTHER INFORMATION: Decoy-Oligonucleotide

<400> SEQUENCE: 22
agccagccag                                                          10

<210> SEQ ID NO 23
<211> LENGTH: 16
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (9)..(9)
<223> OTHER INFORMATION: Y=c or t

<400> SEQUENCE: 23
tccctggcyg gctgac                                                   16

<210> SEQ ID NO 24
<211> LENGTH: 16
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (8)..(8)
<223> OTHER INFORMATION: R=a or g

<400> SEQUENCE: 24
gtcagccrgc caggga                                                   16

<210> SEQ ID NO 25
<211> LENGTH: 13
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (6)..(6)
<223> OTHER INFORMATION: Y=c or t

<400> SEQUENCE: 25
ctggcyggct gac                                                      13

<210> SEQ ID NO 26
<211> LENGTH: 13
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (8)..(8)
<223> OTHER INFORMATION: R=a or g

<400> SEQUENCE: 26
gtcagccrgc cag                                                      13

<210> SEQ ID NO 27
<211> LENGTH: 16
```

```
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (6)..(7)
<223> OTHER INFORMATION: B=g or t or c
<220> FEATURE:
<221> NAME/KEY: misc_feature
<222> LOCATION: (11)..(11)
<223> OTHER INFORMATION: B=g or t or c
<220> FEATURE:
<221> NAME/KEY: misc_feature
<222> LOCATION: (9)..(9)
<223> OTHER INFORMATION: Y=c or t

<400> SEQUENCE: 27
tccctbbcyg bctgac                                                    16

<210> SEQ ID NO 28
<211> LENGTH: 16
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (6)..(6)
<223> OTHER INFORMATION: V=g or c or a
<220> FEATURE:
<221> NAME/KEY: misc_feature
<222> LOCATION: (10)..(11)
<223> OTHER INFORMATION: V=g or c or a
<220> FEATURE:
<221> NAME/KEY: misc_feature
<222> LOCATION: (8)..(8)
<223> OTHER INFORMATION: R=a or g

<400> SEQUENCE: 28
gtcagvcrgv vaggga                                                    16

<210> SEQ ID NO 29
<211> LENGTH: 13
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (5)..(6)
<223> OTHER INFORMATION: B=g or t or c
<220> FEATURE:
<221> NAME/KEY: misc_feature
<222> LOCATION: (10)..(10)
<223> OTHER INFORMATION: B=g or t or c
<220> FEATURE:
<221> NAME/KEY: misc_feature
<222> LOCATION: (8)..(8)
<223> OTHER INFORMATION: Y= c or t

<400> SEQUENCE: 29
ccctbbcygb ctg                                                       13

<210> SEQ ID NO 30
<211> LENGTH: 13
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (4)..(4)
```

```
<223> OTHER INFORMATION: V=g or c or a
<220> FEATURE:
<221> NAME/KEY: misc_feature
<222> LOCATION: (8)..(9)
<223> OTHER INFORMATION: V=g or c or a
<220> FEATURE:
<221> NAME/KEY: misc_feature
<222> LOCATION: (6)..(6)
<223> OTHER INFORMATION: R=a or g

<400> SEQUENCE: 30
cagvcrgvva ggg                                                          13

<210> SEQ ID NO 31
<211> LENGTH: 13
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (3)..(4)
<223> OTHER INFORMATION: B=g or t or c
<220> FEATURE:
<221> NAME/KEY: misc_feature
<222> LOCATION: (8)..(8)
<223> OTHER INFORMATION: B=g or t or c
<220> FEATURE:
<221> NAME/KEY: misc_feature
<222> LOCATION: (6)..(6)
<223> OTHER INFORMATION: Y=c or t

<400> SEQUENCE: 31
ctbbcygbct gac                                                          13

<210> SEQ ID NO 32
<211> LENGTH: 13
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (6)..(6)
<223> OTHER INFORMATION: V=g or c or a
<220> FEATURE:
<221> NAME/KEY: misc_feature
<222> LOCATION: (10)..(11)
<223> OTHER INFORMATION: V=g or c or a
<220> FEATURE:
<221> NAME/KEY: misc_feature
<222> LOCATION: (8)..(8)
<223> OTHER INFORMATION: R=a or g

<400> SEQUENCE: 32
gtcagvcrgv vag                                                          13

<210> SEQ ID NO 33
<211> LENGTH: 10
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (3)..(4)
<223> OTHER INFORMATION: B=g or t or c
<220> FEATURE:
<221> NAME/KEY: misc_feature
<222> LOCATION: (8)..(8)
<223> OTHER INFORMATION: B=g or t or c
<220> FEATURE:
<221> NAME/KEY: misc_feature
```

```
<222> LOCATION: (6)..(6)
<223> OTHER INFORMATION: Y=c or t

<400> SEQUENCE: 33 ctbbcygbct                                                            10

<210> SEQ ID NO 34
<211> LENGTH: 10
<212> TYPE: DNA
<213> ORGANISM: Artificial Sequence
<220> FEATURE:
<223> OTHER INFORMATION: Decoy-Oligonucleotide
<220> FEATURE:
<221> NAME/KEY: misc_feature
<222> LOCATION: (3)..(3)
<223> OTHER INFORMATION: V=g or c or a
<220> FEATURE:
<221> NAME/KEY: misc_feature
<222> LOCATION: (7)..(8)
<223> OTHER INFORMATION: V=g or c or a
<220> FEATURE:
<221> NAME/KEY: misc_feature
<222> LOCATION: (5)..(5)
<223> OTHER INFORMATION: R=a or g

<400> SEQUENCE: 34 agvcrgvvag                                                            10

<210> SEQ ID NO 35
<211> LENGTH: 21
<212> TYPE: DNA
<213> ORGANISM: Artificial Sequence
<220> FEATURE:
<223> OTHER INFORMATION: Decoy-Oligonucleotide

<400> SEQUENCE: 35
gagtctggcc aacacaaatc c                                               21

<210> SEQ ID NO 36
<211> LENGTH: 21
<212> TYPE: DNA
<213> ORGANISM: Artificial Sequence
<220> FEATURE:
<223> OTHER INFORMATION: Decoy-Oligonucleotide

<400> SEQUENCE: 36
gacctctagg gtcatgcagg t                                               21

<210> SEQ ID NO 37
<211> LENGTH: 19
<212> TYPE: DNA
<213> ORGANISM: Artificial Sequence
<220> FEATURE:
<223> OTHER INFORMATION: DNA Oligonucleotide

<400> SEQUENCE: 37
gggtcagccg gccagggaa                                                  19

<210> SEQ ID NO 38
<211> LENGTH: 21
<212> TYPE: DNA
<213> ORGANISM: Artificial Sequence
<220> FEATURE:
<223> OTHER INFORMATION: DNA Oligonucleotide

<400> SEQUENCE: 38
agcttgatgc cctggtggga g                                               21
```

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
ggaacctgtg tgaccctc                                                   18

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
ccacgtcata ctcatcca                                                   18

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
gtactccaca ttcctacttc t                                               21

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
tttgggtcta ttccgttgtg tc                                              22

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
ggacacccat cccaaatcag tc                                              22

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
cacggtgaaa tactgcctgg tg                                              22

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
tcaccatctt ccaggagcg					19

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
ctgcttcacc accttcttga					20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
gttcatccgg caccagtcag					20

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
acgtgcacat gagctgccta c					21

<210> SEQ ID NO 49
<211> LENGTH: 21
<212> TYPE: DNA
<213> ORGANISM: Artificial Sequence
<220> FEATURE:
<223> OTHER INFORMATION: Decoy-Oligonucleotide

<400> SEQUENCE: 49
cctgcattct gggaactgta g					21

<210> SEQ ID NO 50
<211> LENGTH: 21
<212> TYPE: DNA
<213> ORGANISM: Artificial Sequence
<220> FEATURE:
<223> OTHER INFORMATION: Decoy-Oligonucleotide

<400> SEQUENCE: 50
cctgtatgcc gtgagctata g					21

<210> SEQ ID NO 51
<211> LENGTH: 19
<212> TYPE: DNA
<213> ORGANISM: Artificial Sequence
<220> FEATURE:
<223> OTHER INFORMATION: Decoy-Oligonucleotide

<400> SEQUENCE: 51
gccggctgac cctgcctca					19

<210> SEQ ID NO 52

```
<211> LENGTH: 19
<212> TYPE: DNA
<213> ORGANISM: Artificial Sequence
<220> FEATURE:
<223> OTHER INFORMATION: Decoy-Oligonucleotide

<400> SEQUENCE: 52
tcttccctag ctgactgac                                                  19

<210> SEQ ID NO 53
<211> LENGTH: 16
<212> TYPE: DNA
<213> ORGANISM: Artificial Sequence
<220> FEATURE:
<223> OTHER INFORMATION: Decoy-Oligonucleotide

<400> SEQUENCE: 53
tccctgaccg actcag                                                     16

<210> SEQ ID NO 54
<211> LENGTH: 16
<212> TYPE: DNA
<213> ORGANISM: Artificial Sequence
<220> FEATURE:
<223> OTHER INFORMATION: Decoy-Oligonucleotide

<400> SEQUENCE: 54
tccctagctg actgac                                                     16

<210> SEQ ID NO 55
<211> LENGTH: 27
<212> TYPE: DNA
<213> ORGANISM: Artificial Sequence
<220> FEATURE:
<223> OTHER INFORMATION: Decoy-Oligonucleotide

<400> SEQUENCE: 55
gtgcatttcc cgtaaatctt gtctaca                                         27

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
ctgggaactg tagtttccct ag                                              22

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
accctgtcat tcagtgacgc ac                                              22

<210> SEQ ID NO 58
<211> LENGTH: 22
<212> TYPE: DNA
<213> ORGANISM: Artificial Sequence
<220> FEATURE:
<223> OTHER INFORMATION: DNA Oligonucleotide

<400> SEQUENCE: 58
```
gctcccacca gggcatcaag ct                                          22

<210> SEQ ID NO 59
<211> LENGTH: 16
<212> TYPE: DNA
<213> ORGANISM: Artificial Sequence
<220> FEATURE:
<223> OTHER INFORMATION: DNA Oligonucleotide

<400> SEQUENCE: 59
ttccctggcc ggctga                                                 16

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
ggatgtggct gtctgcatgg ac                                          22

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
tggtccacga tggtgacttt gg                                          22

<210> SEQ ID NO 62
<211> LENGTH: 24
<212> TYPE: DNA
<213> ORGANISM: Artificial Sequence
<220> FEATURE:
<223> OTHER INFORMATION: Primer

<400> SEQUENCE: 62
gaccacagtc catgccatca ctgc                                        24

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
atgaccttgc ccacagcctt gg                                          22

<210> SEQ ID NO 64
<211> LENGTH: 100
<212> TYPE: DNA
<213> ORGANISM: Artificial Sequence
<220> FEATURE:
<223> OTHER INFORMATION: Primer

<400> SEQUENCE: 64
ctggtgtacc ccacctgcat tctgggaact gtagtttccc tagtccccca tgctcccacc    60
agggcatcaa gctcttccct ggccggctga ccctgcctca                         100

<210> SEQ ID NO 65

-continued

```
<211> LENGTH: 10
<212> TYPE: DNA
<213> ORGANISM: Artificial Sequence
<220> FEATURE:
<223> OTHER INFORMATION: Primer

<400> SEQUENCE: 65
ctagctgact                                                          10
```

FUNCTIONAL CORRECTION OF THE $^{-786}$C/T-VARIANCE OF THE HUMAN ENOS-GENE

This application claims priority to PCT/DE 03/03028, filed on Sep. 12, 2003, the entire contents of which are hereby incorporated by reference.

The present invention relates to decoy oligonucleotides with the nucleic acid sequence according to SEQ ID NO: 1 to 34 and their use as pharmaceutical agents. The present invention also discloses a method for diagnosis of the $^{-786}$C/T-variance in the eNOS-gene.

One substantial goal of deciphering the human genome is to identify pathogenic genes (on the basis of the method of action of the products) and/or to identify pathogenic changes in the structure of these genes (polymorphisms) and to allocate them to a disease profile. As a result, the causal treatment of a plurality of diseases is brought closer, if one accepts that these diseases are caused by a defined number of gene products expressed too strongly, too weakly or incorrectly. Although the generally singular genetic defect (monogenetic disease) is already known for certain inherited diseases (e.g. mucoviscidosis), the situation is considerably more complex for polygenetic diseases (e.g. atherosclerosis). The coincidence of various genetic defects does indeed predestine the affected person for the disease, but the disease only develops on exposure to certain environmental factors. Regardless of this, the targeted intervention into the expression of one or more genes does offer the opportunity for a cause-related and not merely symptom-related therapy even for polygenetic disorders.

In the industrial nations, atherosclerosis, with its primary consequential diseases, cardiac infarction, heart failure, kidney failure and stroke, is responsible for more than 50% of all deaths, and this trend is continuing to rise. By 2020, atherosclerosis-related cardiovascular diseases will represent the most frequent cause of death worldwide, not least because of the increase in life expectancy. Alongside the presumed genetic predisposition, high blood pressure, hypercholesterolaemia, smoking and diabetes (type I and II) are amongst the primary risk factors for atherosclerosis. With the exception of the predisposition and (cigarette) smoking, these can be treated medicinally, but this treatment is generally only initiated when the affected persons have become symptomatic, that is to say, when manifest atheromatous plaques are present in the arterial walls, especially in the coronary blood vessels, the carotids and cerebral blood vessels and renal blood vessels. Often, the only therapy option for the avoidance of a cerebral, myocardial or renal infarction is to expand the blocked arteries using a balloon catheter with or without subsequent placing of a vascular support (stent), or the bypass operation, in which the blocked artery is bypassed using autologous arterial or venous segments. One problem with these interventions, alongside the high rate of re-closure of the treated the vessel (approximately 30% for balloon catheter/stent after 6-12 months, and approximately 50% for the aorto-coronary venous bypass after 1-5 years), is the fact that atherosclerosis must be considered as an underlying systemic disease, which can manifest at any time in a part of the vascular system not previously affected.

Chronic inflammatory and autoimmune diseases present an even greater medical problem in view of the associated morbidity, rather than mortality, and under some circumstances, the need for lifelong therapy. Moreover, the strong-acting anti-inflammatory agents such as glucocorticoids (e.g. prednisone), immunosuppressants (e.g. cyclosporin A) and antimetabolites (e.g. azathioprine), which are generally administered systemically to this patient group, sometimes cause serious side-effects. These include, in particular, myelotoxicity, neurotoxicity, nephrotoxicity, metabolic disorders and even the induction of diabetes, arterial hypertension, infections and malignancies. For example, 25% of patients with rheumatoid arthritis, who are treated with the cytostatic agent methotrexate, develop severe cirrhosis of the liver within 2 years. The numerically most important chronic inflammatory and/or autoimmune diseases include chronic obstructive bronchitis and pulmonary emphysema (referred to together as chronic obstructive pulmonary diseases or COPD; prevalence in Germany 4-7%), psoriasis (2-3%), rheumatoid arthritis (chronic polyarthritis; 0.8%) and insulin-dependent diabetes (type I; 0.5%). Presumably on the basis of various genetic predispositions, these diseases are attributable an immune regulatory disturbance in the form of an excessive activation of type 1 T-helper cells (Th1).

The infiltration of these immune cells into the vascular wall also plays an important role in the pathogenesis of atherosclerosis. Further examples of a hyperactivation of Th1 cells are the rejection of transplants, contact dermatitis and persistent consequential diseases from bacterial or viral infection.

The present invention is therefore based on the object of providing means for a prevention, treatment or diagnosis of the named diseases. This object is achieved by the subject matter defined in the patent claims.

The invention will be described in greater detail with reference to the following diagrams:

FIG. 1 shows the sequence of the human nitric oxide (NO)-synthase (eNOS)-gene in the region of the T to C transition at position −786 (SEQ ID NO:64). The underlined bases indicate the consensus binding sites for two known transcription factors.

FIG. 2 shows, in the form of bar charts, the absence of stimulability of eNOS expression with reference to (A) mRNA (n=8-12) and (B) protein level (n=3) in cultivated endothelial cells isolated from the umbilical vein of donors with the $^{-786}$C/C-genotype, by comparison with endothelial cells from donors with the $^{-786}$C/T and, in particular, the $^{-786}$T/T-genotype. The diagram illustrates the percentage increase in the expression of cells, which were exposed for 24 hours (mRNA) or respectively 36 hours (protein) in a cone/plate viscometer to a wall-shear-stress (WSS) of 30 dyn/cm$^2$, by comparison with cells from the same donor, which were incubated for this period under static conditions (*P<0.05 by comparison with the static control).

Figure 3:
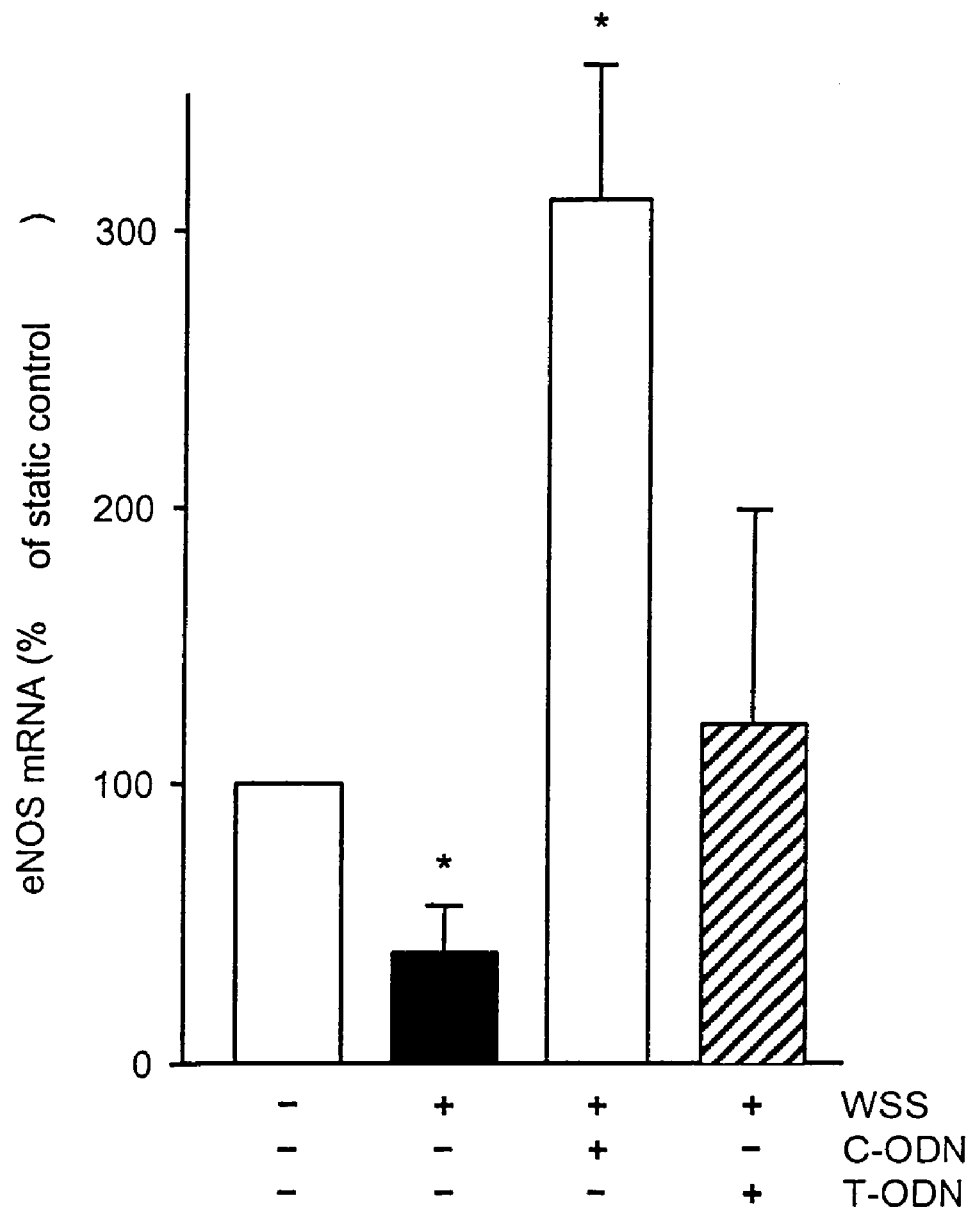

FIG. 3 shows, in the form of a bar chart, the restoration of shear-stress induction of the eNOS-expression in cultivated endothelial cells from donors with the $^{-786}$C/C genotype previously treated for 4 hours with a C-type (SEQ ID NO:1) but not with a T-type allele decoy oligonucleotide (SEQ ID NO: 3) (concentration in the medium of 10 µmol/l). The diagram shows the percentage increase in mRNA expression in cells, which had been exposed for 24 hours in a cone/plate viscometer to a wall shear stress (WSS) of 30 dyn/cm$^2$, by comparison with cells from the same donor, which were incubated for this period under static conditions (n=4; *P<0.05 by comparison with the static control).

Figure 4:
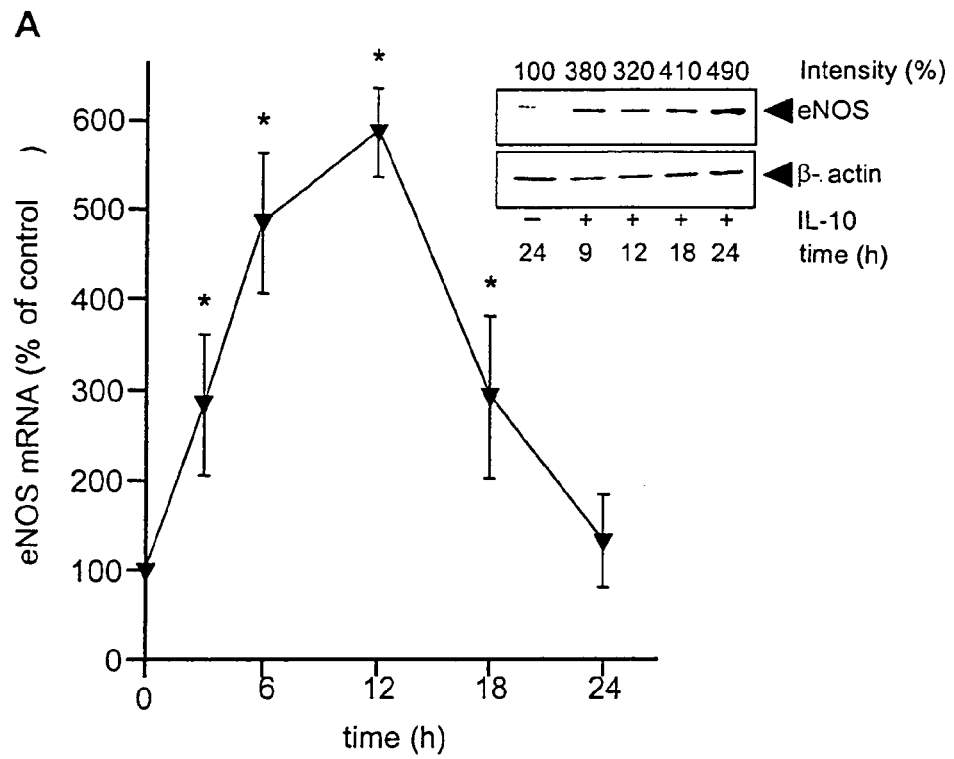
Figure 4:
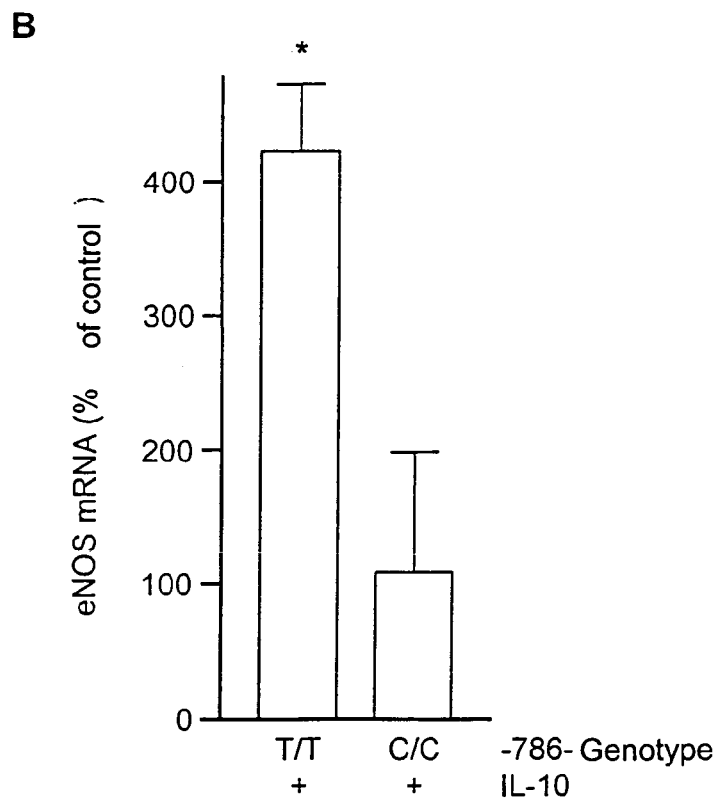

FIG. 4 shows, in a graphic representation and a representative Western-blot analysis, the time-dependent induction of the eNOS expression of mRNA (statistical summary, n=3-10, *P<0.05 vs. non-stimulated cells) and protein level by IL-10 (2 ng/ml) in cultivated endothelial cells from donors with $^{-786}$T/T-genotype, who had previously been treated for 9 hours with vitamin D3 (10 nmol/l), in order to stimulate the expression of the IL-10 receptor. FIG. 4 (B) shows, in the form of a bar chart, the absence of induction of eNOS-expression by IL-10 under otherwise identical experimental conditions in cultivated endothelial cells from donors with $^{-786}$C/C-genotype (statistical summary, n=6, *P<0.05 vs. non-stimulated cells).

Figure 5:
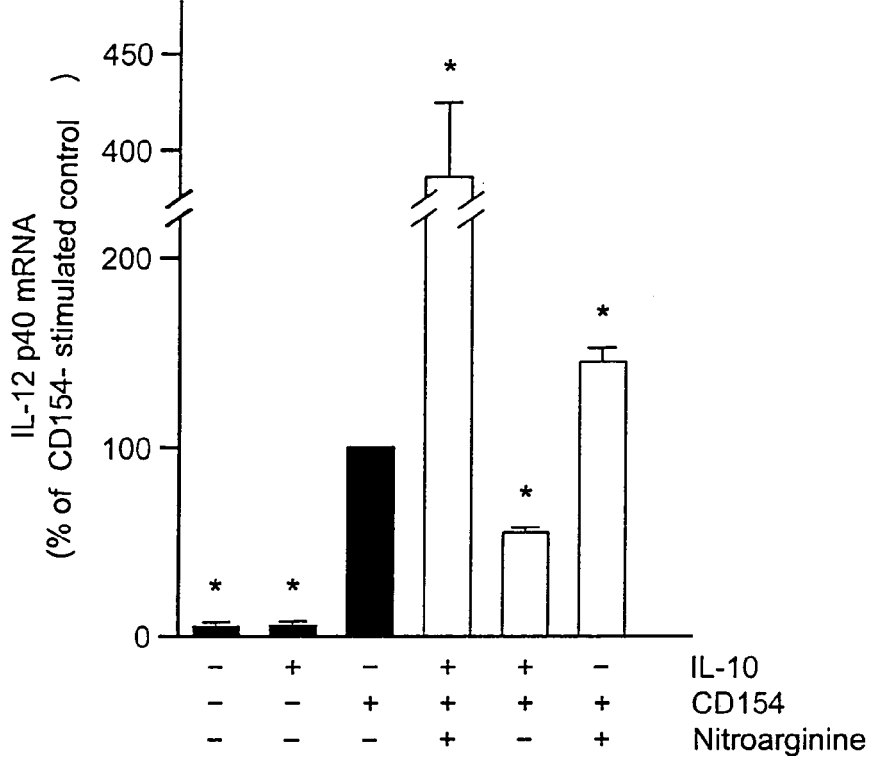
Figure 5:
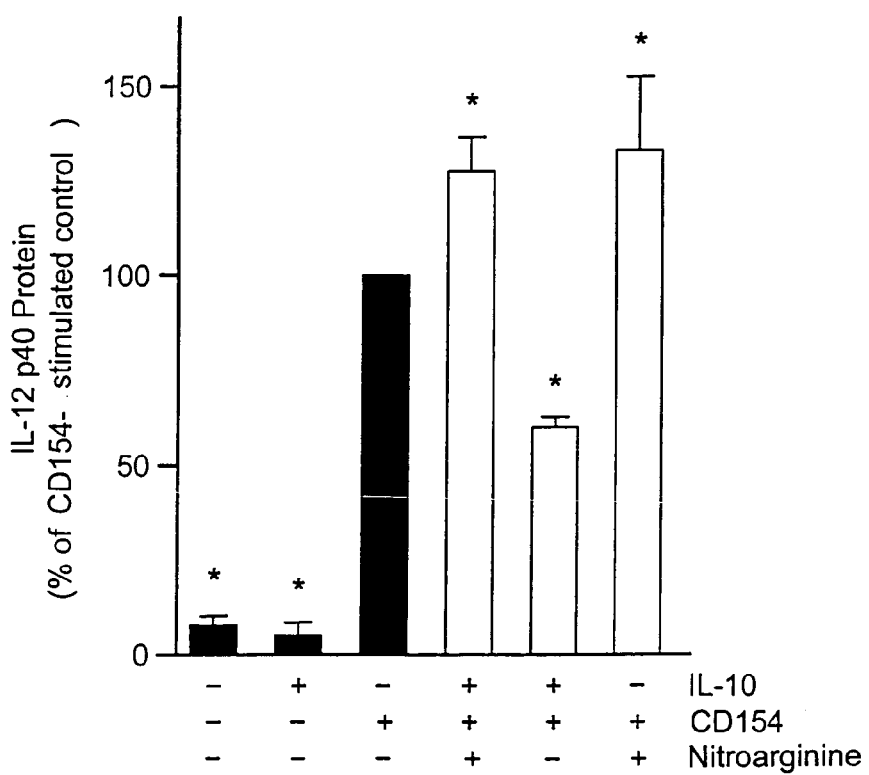

FIG. 5 shows, in the form of bar charts, the effects of the IL-10 (2 nm/ml) induced intensified eNOS expression on the CD154-stimulated (2×10$^5$ mouse myeloma cells/ml) de novo synthesis of IL-12 p40 on (A) mRNA and (B) protein level over 6 hours in IL-10 receptor-expressing, cultivated endothelial cells from donors with $^{-786}$T/T or respectively $^{-786}$C/T-genotype and their modulation by means of blockade of the eNOS activity with nitroarginine. Statistical summaries of the RT-PCR analyses (with rpl32 as internal standard; n=6) and ELISA-data (n=6-10; *P<0.05 vs. CD154-stimulated control cells).

Figure 6:
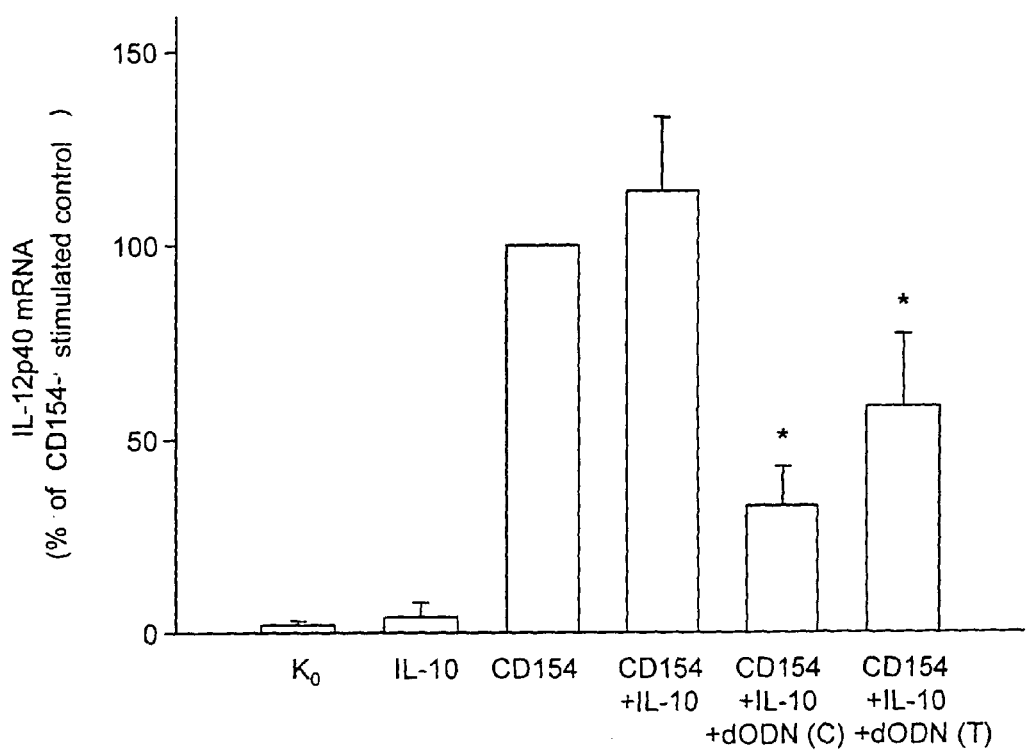

FIG. 6 shows, in the form of a bar chart, the absence of inhibition of the CD154-stimulated IL-12 p40 expression in IL-10 receptor-expressing cultivated endothelial cells from donors with the $^{-786}$C/C-genotype and their restoration by previous treatment of the cells (4 hours, 10 µmol/l) with the C-type-allele decoy oligonucleotide (SEQ ID NO: 5). Statistical summary of the RT-PCR analyses (with rpl32 as internal standard; n=7-15, *P<0.05 vs. CD154-stimulated control cells).

Figure 7:
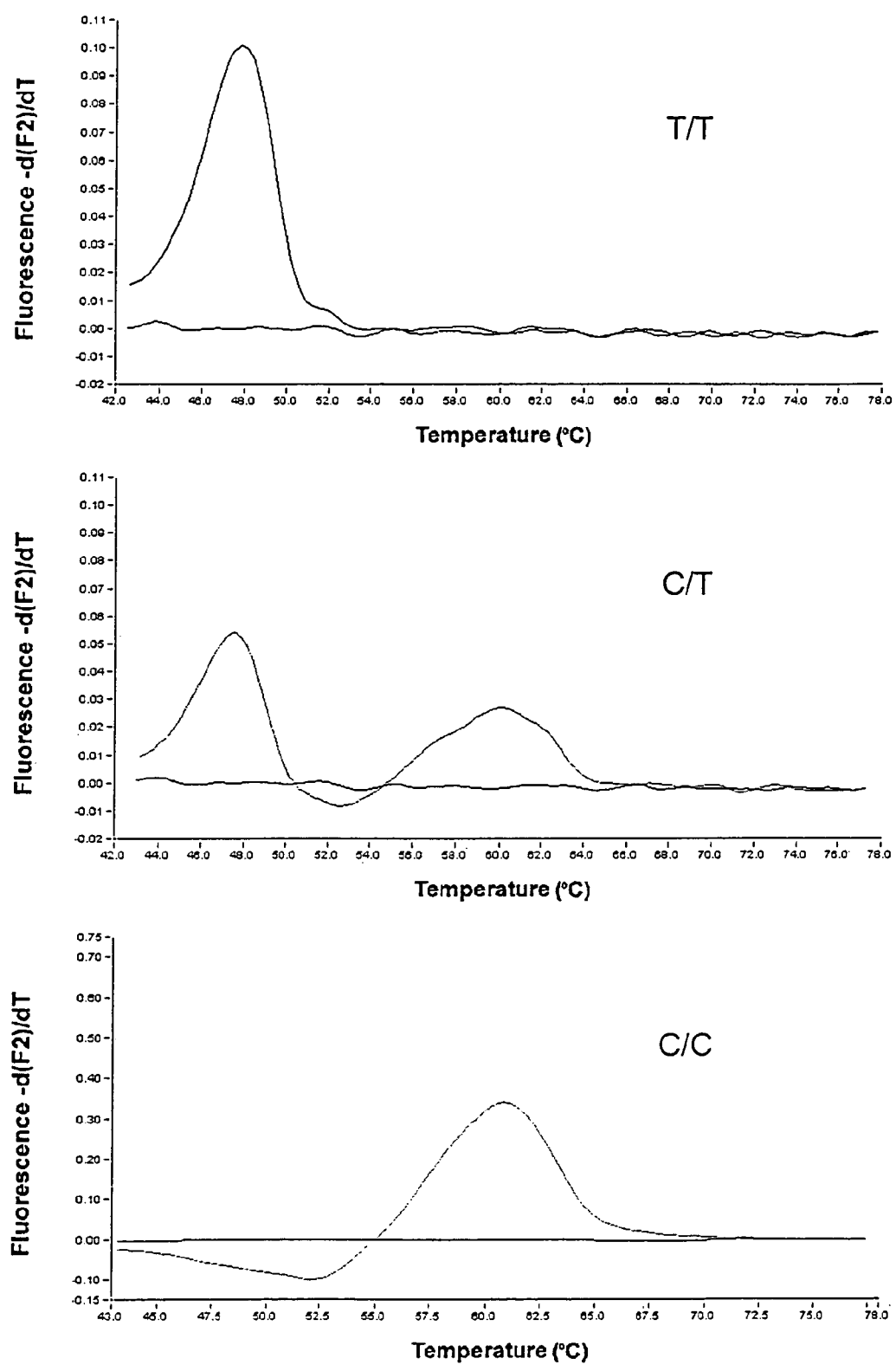

FIG. 7 shows, in exemplary graphic representations, the results of the real-time-PCR/fluorescence resonance energy transfer (FRET)/DNA-melting curve analysis as developed for the genotyping of the three variants of the $^{-786}$C/T-polymorphism of the human eNOS gene.

Figure 8:
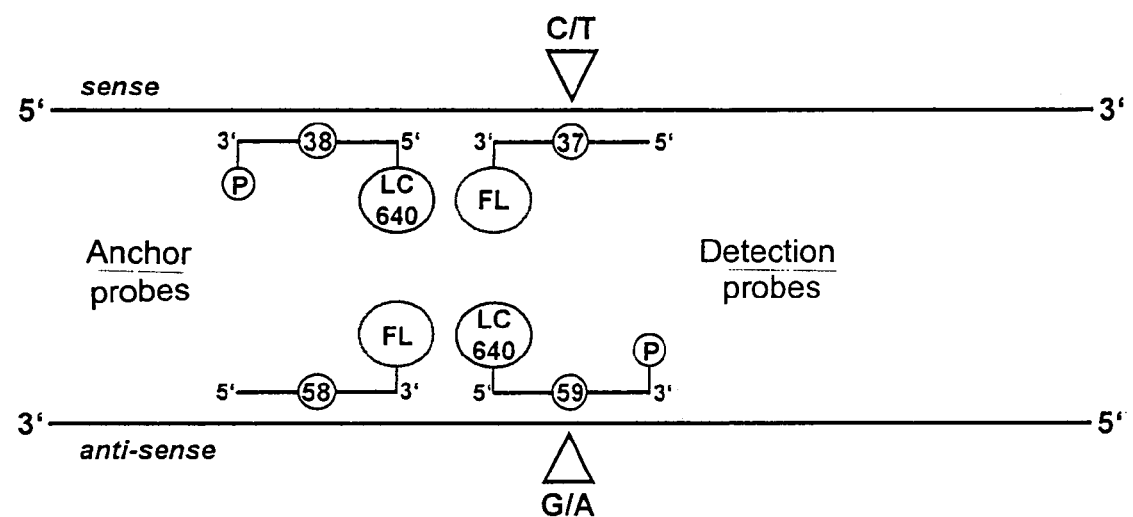

FIG. 8 shows schematically two variants of the real-time-PCR/FRET/DNA-melting curve analysis for the diagnosis of the $^{-786}$C/T-variance in the eNOS gene. The circled numbers represent the SEQ ID NO of the anchor or detection probes (FL, fluorescein; LC 640, LC-Red 640) according to the invention.

The terms "decoy oligonucleotide" or "cis-element decoy" used in the present document refer to a double-strand DNA molecule, which provides a sequence, which corresponds to or is similar to the natural core-binding sequence of a DNA-binding protein or protein complex in the genome, and to which the protein or the protein complex in the cell binds. In the sense of the present invention, the cis-element decoy therefore acts as a molecule for the competitive inhibition (or rather neutralisation) of the protein or protein complex, which blocks the expression of the eNOS, a gene with a demonstrably important protective function, in the presence of the $^{-786}$C/C-genotype and therefore acts in a predisposing manner for the development of the diseases and complications defined in the patent claims.

The term "C/T-variance" used in the present document refers to the presence of a heterozygotic or homozygotic T to C transition at position −786 of the human eNOS gene. Accordingly, the term "C/C-genotype" is the homozygotic T to C transition and the "C/T-genotype" is the heterozygotic T to C transition.

The synthesis of nitric oxide (NO) by the endothelial cells of the vascular wall plays an important role in the regulation of organ circulation and the maintenance of vascular wall integrity. The latter effect of NO is based, in particular, on inhibiting the proliferation of smooth vascular muscle cells. Moreover, NO inhibits the expression of chemokines and cell-adhesion molecules in the endothelium. As a result, in the case of inflammatory processes, the recruitment, activation and transmigration of leukocytes circulating in the blood is suppressed. To this extent, an important role in the prevention of atherosclerosis, which, according to current understanding, represents a chronic recurrent inflammatory disease, is attributed inter alia to NO.

The formation of NO in the endothelial cells is catalysed by the so-called endothelial NO-synthase (eNOS); the physiologically most important stimulus for the activity of the enzyme is a change in the wall shear stress. That is, the viscous tensile stress exerted by the flowing blood on the endothelial cells, which line the interior of the arteries and veins. Accordingly, an increase in the wall shear stress, triggered by a constriction of the blood vessel or an increase in the blood flow leads to an increase in NO-synthase activity and, as a result, to an NO-mediated vasodilation, i.e. a increase of organ circulation. Alongside this acute change of enzyme activity, an increase in the wall shear stress also leads in the medium term to an intensified expression of NO-synthase in the endothelial cells. Determined by the constant local changes in wall shear stress, the shear-stress-induced induction (or rather maintenance) of NO-synthase-expression is of critical importance for the NO-synthesis capacity of the vascular endothelium and accordingly for the structural and functional integrity of the vascular wall (Gimbrone et al. (2000) Ann. N.Y. Acad. Sci. 920, 230).

Interleukin-10 (IL-10) is an important anti-inflammatory cytokine in chronically recurring inflammatory diseases such as psoriasis, rheumatoid arthritis or Crohn's disease, which are caused by an excessive activation of the T-helper cells type 1 (Moore et al. (2001) Annu. Rev. Immunol. 19, 683). The infiltration and activation of Th1-cells in the vascular wall also plays an important role in the pathogenesis of atherosclerosis (Daugherty and Rateri (2002) Circ. Res. 90, 1039). IL-10 inhibits the formation of IL-12 in the antigen-presenting cells communicating with the Th1 cells. These include, in particular, dendritic cells and monocytes/macrophages; but endothelial cells are also capable of expressing the MHC II-molecule required for antigen presentation on their surface and releasing biologically active IL-12. IL-12 itself is the most important factor for the differentiation of naïve T-helper cells to form Th1 cells and stimulates their proliferation (clonal expansion). Interestingly, the synthesis of IL-12 in human endothelial cells can only be induced after co-stimulation via the CD40 receptor/CD40-ligand system (Lienenlüke et al. (2000) Eur. J. Immunol. 30, 2864). In this context, the endothelial cells generally express the receptor (CD40), and activated Th1-cells express the CD40-ligand (also referred to as CD154).

The human eNOS gene provides a series of polymorphisms, in which a single base is exchanged (SNP stands for single nucleotide polymorphism) also, for example, a T to C transition in the promoter of the gene at position −786 (FIG. 1). Linkage analyses show that this base exchange does not occur in isolation, but is always associated with an A to G transition at position −922 and a T to A transition at position −1486. The functional significance of these polymorphisms is so far unknown, with the exception of the T to C transition at position −786, which has now been explained by the inventors, (Wattanapitayakul et al. 2001 Trends Pharmacol. Sci. 22, 361). It is remarkable that in Western Europe, as in the Caucasian population of North America, 12-15% are homozygotic carriers of the −786-variant, that is to say they have the genotype .sup.−786C/C. Approximately 48% are heterozygotic for this SNP, that is to say, they have the genotype .sup.−786C/T, and approximately 38% are homozygotic carriers of the .sup.−786T-variant, that is to say they have the genotype .sup.−786T/T. It is also interesting that this mutation evidently does not occur in other mammals (dog, mouse, rat and cattle), because a base is missing at the corresponding position in the eNOS promoter in these species.

The term coronary heart disease, abbreviated as CHD, is understood to mean the (manifest) atherosclerosis formed in the coronary blood vessels (coronary arteries), which leads to a progressive narrowing of the effected blood vessels. The consequences of this circulatory disturbance in the coronary arteries are (in ascending order depending on the degree of severity) stable angina pectoris (the atherosclerosis-determined circulation disturbance is at least partially compensated by the formation of collateral arteries, or so-called collaterals; patients only show symptoms under physical stress, e.g. the occurrence of chest pains); unstable angina pectoris (increasing narrowing of the arteries caused by thrombosis); patients have chest pains even while resting, approximately 25% suffer myocardial infarction within 4 weeks); myocardial infarction itself (total occlusion of coronary artery by a thrombosis) and sudden cardiac death (severe circulatory disorders resulting from acute occlusion of one or more coronary blood vessels with cardiac-rhythm disturbances, which lead to cardiac arrest). Coronary heart disease and coronary insufficiency triggered by it (deficient supply of the cardiac muscle with oxygen caused by deficient circulation) is also primarily responsible for the intensity of myocardial weakness (heart failure). Accordingly, coronary heart disease continues to be the most frequent cause of death in the western industrial nations, and the discovery of genetic risk factors for the development of coronary heart disease is of major socio-economic importance.

The very rare, spontaneous spasmodic condition of one or more coronary blood vessels (also referred to as coronary spasm, vasospastic angina pectoris or Prinzmetal-angina) differs from CHD in that the spontaneous spasm represents the extreme form of a dynamic coronary stenosis (eccentric stenosis with constriction of the plaque-free vascular wall) in patients with unstable angina pectoris. Patients with vasospastic angina pectoris are often smokers and generally have other vascular phenomena (migraine, Raynaud's syndrome). The pathogenesis of vasospastic angina pectoris has still not been explained. A participation of the autonomous nervous system is presumed.

The inventors have surprisingly found that—regardless of the other primary risk factors for atherosclerosis in the coronary blood vessels, i.e. high blood pressure, hypercholesterolaemia, smoking and diabetes—carriers of the $^{-786}$C/C-genotype of the eNOS gene are subject to a more rapid progression of coronary heart disease (Table 1). For example, 19.0% of CHD-positive patients have the $^{-786}$C/C-genotype; but only 4.4% of CHD-negative patients; the frequency of occurrence of the $^{-786}$C/C-genotype in the control population is 11.8%. Accordingly, these patients have a significantly increased risk of suffering prematurely from a potentially fatal myocardial infarction. The reason for the more rapid manifestation of atherosclerosis in homozygotic carriers of the genetic defect is a reduced NO-synthesis capacity of the endothelial cells.

Accordingly, the inventors were able to demonstrate that in cultivated endothelial cells, which had been isolated from the umbilical vein of donors with the $^{-786}$C/C-genotype, the typical increase of eNOS-expression with reference to mRNA and also protein level caused by an increase in wall shear stress does not occur (FIG. 2). The data for the expression of eNOS mRNA obtained by means of conventional RT-PCR were confirmed in full using a quantitative real-time PCR analysis (T/T-genotype 454±27% of the statistical control, P<0.05; C/T-genotype 278±27%, P<0.05; C/C-genotype 116±26%; n=8-12). By contrast, in endothelial cells from donors with the $^{-786}$C/C genotype, a significant increase in the expression of eNOS was triggered by increasing the wall shear stress, if the cells had previously been treated with a 22 bp long decoy oligonucleotide, which corresponds to the C-type (SEQ ID NO: 1) but not to the T-type allele (SEQ ID NO 3) of the eNOS gene. These findings obtained using conventional RT-PCR were also confirmed in full using quantitative real-time PCR analysis (WSS 117±27% of the statistical control; WSS plus C-type decoy oligonucleotide 324±30%, P<0.05; WSS plus T-type decoy oligonucleotide 133±47%; n=4).

The transcription is controlled by proteins, which bind to a starter region of a gene (promoter region). The correct congregation of several of these transcription factors (transcriptosomes) leads to an activation of the RNA-polymerase and initiates the transcription. Conversely, the binding of an incorrect transcription factor can prevent the formation of the transcriptosome and therefore block the expression of the gene. Decoy oligonucleotides initiate the sequence motif, to which the target transcription factor binds in the starter region of its target gene (target genes), and neutralise the it. In consequence, the induction and/or repression of the transcription mediated by this transcription factor is prevented.

In V. saphena segments of patients, who had to undergo an aorto-coronary bypass operation, it was shown that the endothelium-dependent NO-mediated vasodilation is significantly less pronounced in individuals with $^{-786}$C/C-genotype (n=13) regardless of the presence of the primary risk factors for atherosclerosis, (maximum response to acetylcholine reduced by 35%, P<0.05) than in carriers of the two other genotypes (n=41 and 45 respectively). This finding supports the hypothesis that the deficient shear stress-induced maintenance of the eNOS-expression in homozygotic carriers of the genetic defect limits the NO-synthesis capacity of the vascular endothelium, and to this extent hastens manifestation of atherosclerosis.

Furthermore, the inventors have found that, after exposure to various pro-inflammatory cytokines, i.e. under (simulated) inflammatory conditions, and also after treatment with vitamin D3, human endothelial cells express the receptor for IL-10. The stimulation of the receptor, i.e. incubation of cells expressing the IL-10 receptor with IL-10, resulted in a significant increase in the eNOS-expression in the endothelial cells (FIG. 4); an effect which was attributed, on the basis of electrophoretic mobility-shift analyses and with the use of a corresponding decoy oligonucleotide, to the activation of the transcription factor: signal transducer and activator of transcription (STAT)-3. One functional consequence of this IL-10-mediated increase in eNOS expression was the inhibition of the CD154-induced new synthesis of IL-12 in the endothelial cells (FIG. 5), which is NO-sensitive (modulation by the NO-synthase-inhibitor nitroarginine). Accordingly, IL-10 can exert its anti-inflammatory effect in Th1-weighted chronic inflammatory disorders, especially the inhibition of IL-12 synthesis in the endothelial cells, by increasing the eNOS expression and the associated intensified formation of NO.

The STAT-binding position in the promoter of the human eNOS-gene, which is important for the IL-10 effect, is disposed approximately 60 base pairs above the T to C transition at position −786. The inventors have shown that the $^{-786}$C/T polymorphism has an effect on the inducibility of eNOS-expression by IL-10. For example, in endothelial cells from donors with the $^{-786}$C/C-genotype—in spite of vitamin D3-induction of the IL-10 receptor expression—there was no increase in eNOS expression as a result of IL-10 (FIG. 4). Beyond this, the IL-10 exposure did not inhibit the CD154-induced synthesis of IL-12 in the cells, but tended rather to intensify it (FIG. 6). In dependence upon spatial proximity, there is an inhibition of the formation of the transcriptosome in the region of the STAT binding position by the inhibitory transcription factor binding at position $-786$. Experimental data confirm that this deficit, that is to say, the absence of induction of eNOS-expression by IL-10 and consequently the absence of IL-10 mediated inhibition of IL-12 synthesis can be fully compensated by prior treatment of the endothelial cells with the C-type-allele decoy oligonucleotide (SEQ ID NO: 1 and SEQ ID NO: 5) (FIG. 6) described above.

A further comparative genotyping in the context of the absence of inducibility of eNOS expression by IL-10 shows that Caucasian patients with rheumatoid arthritis exhibit a significantly greater prevalence of the $-786$C/C-genotype than in the normal population (17.0% by comparison with 11.8%, Table 2). With these patients, for example, the intra-articular application of a decoy oligonucleotide during the inflammatory phase can intensify the endogenous IL-10-mediated inhibition of the Th1-cell response in the long term and/or render this possible in the first place, and can therefore weaken the inflammatory process and the associated cartilage destruction in the relevant joint. For other Th1-weighted chronic inflammatory diseases such as Crohn's disease, there is also a tendency towards a significantly higher prevalence of the $-786$C/C-genotype (Table 2). With diseases of this type, the systemic application of a liposomally packaged decoy oligonucleotide probably offers the maximum possible therapeutic benefit. Other possible applications are presented with reference to the diseases and/or complications additionally defined in the patent claims, wherein respiratory diseases are especially accessible to an inhalative therapy with the decoy oligonucleotides according to the invention; skin disorders are particularly accessible to a topical treatment and explanted organs and/or blood vessels are particularly accessible to an ex vivo incubation treatment, that is to say, outside the receptor organism.

The present invention therefore relates to the provision of a decoy oligonucleotide, which is capable of binding in a sequence-specific manner to a protein or a protein complex (referred to below as "transcription factor" or "inhibitory transcription factor". The sequence of a decoy oligonucleotide, which is used to prevent the binding of the inhibitory transcription factor, is the sequence, to which the transcription factor binds in the promoter of the eNOS gene. The cis-element decoy according to the invention provides the following 10-mer consensus core-binding sequence: 5'-CTBBCYGBCT-3' (SEQ ID NO: 33) wherein Y=C or T and B=C, G or T. The cis-element decoy can, furthermore, be larger than the 10-mer core-binding sequence and can be extended at the 5'-end and/or at the 3'-end. Corresponding mutations in the region of the core-binding sequence (e.g. 5'-CTAGCTGACT-3' (SEQ ID NO:65)) lead to a complete loss of the binding of the transcription factor to the decoy oligonucleotide, evident from the absence of biological effect (Table 3).

Furthermore, the present invention relates to the provision of decoy oligonucleotides, which are capable of binding in a sequence-specific manner to the transcription factor and have one of the following sequences, wherein only one strand of each decoy oligonucleotide is reproduced here, but the complementary strand is also included:

```
                                       (SEQ ID NO: 1)
5'-AGCTCTTCCCTGGCCGGCTGAC-3', (SEQ ID NO: 3)
5'-AGCTCTTCCCTGGCTGGCTGAC-3',
```

-continued
```
                                       (SEQ ID NO: 5)
5'-CTTCCCTGGCCGGCTGACCCTGC-3', (SEQ ID NO: 7)
5'-CTTCCCTGGCTGGCTGACCCTGC-3', (SEQ ID NO: 9)
5'-GCTCTTCCCTGGCCGGCTG-3', (SEQ ID NO: 11)
5'-CAAGCTCTTCCCTGGCCGG-3', (SEQ ID NO: 13)
5'-TCTTCCCTGGCCGGCTGAC-3', (SEQ ID NO: 15)
5'-CTGGCCGGCTGACCCTGCC-3', (SEQ ID NO: 17)
5'-TCCCTGGCCGGCTGAC-3', (SEQ ID NO: 19)
5'-CTGGCCGGCT-3', (SEQ ID NO: 21)
5'-CTGGCTGGCT-3', (SEQ ID NO: 23)
5'-TCCCTGGCYGGCTGAC-3',
wherein Y = C or T, (SEQ ID NO: 25)
5'-CTGGCYGGCTGAC-3',
wherein Y = C or T, (SEQ ID NO: 27)
5'-TCCCTBBCYGBCTGAC-3'
wherein Y = C or T and B = C, G or T, (SEQ ID NO: 29)
5'-CCCTBBCYGBCTG-3'
wherein Y = C or T and B = C, G or T, (SEQ ID NO: 31)
5'-CTBBCYGBCTGAC-3'
wherein Y = C or T and B = C, G or T,
and (SEQ ID NO: 33)
5'-CTBBCYGBCT-3'
wherein Y = C or T and B = C, G or T.
```

Accordingly, the use of the decoy oligonucleotides or cis-element decoys according to the invention, which contain a consensus core-binding position for the inhibitory transcription factor, represents the preferred method for the specific inhibition of the activity of this factor. The exogenous supply of a large number of transcription-factor binding positions to a cell, especially in a larger number than is present within the genome, produces a situation, in which the majority of a given transcription factor binds specifically to the relevant cis-element decoy and not to its endogenous target binding position. This approach for the inhibition of the binding of transcription factors to their endogenous binding position is also referred to as squelching. Squelching (or neutralisation) of transcription factors using cis-element decoys has been successfully used in patients, inter alia in order to inhibit an excessive growth of smooth vascular muscle cells in aorto-coronary venous bypasses. In this context, DNA fragments were used, which contain the specific binding positions for the transcription factor E2F (Mann et al. (1999) Lancet 354, 1493). The present invention accordingly relates to a method for the specific inhibition of the activity of the inhibitory transcription factor, which binds in the promoter region of the eNOS-gene at position −786, comprising the stage of applying of a decoy oligonucleotide according to the present invention. Furthermore, the present invention relates to the decoy oligonucleotides according to the invention as a pharmaceutical agent.

The present invention also relates to the use of the decoy oligonucleotides according to the invention for the manufacture of a pharmaceutical agent, especially for the prevention or therapy of atherosclerosis and its consequential diseases (e.g. coronary heart disease with cardiac infarction and heart failure, cerebral circulation disorders with stroke and/or multi-infarction dementia and peripheral arterial occlusion disease), chronic inflammatory and/or autoimmune diseases such as rheumatoid arthritis (chronic polyarthritis), psoriasis including psoriasis arthritis, allergic contact eczema and atopic eczema (neurodermatitis), chronic inflammatory bowel disorders (in particular, Crohn's disease and ulcerative colitis), diabetes type I and II and their consequential diseases (e.g. diabetic nephropathy, retinopathy and vasculopathy), multiple sclerosis, sarcoidosis, collagenosis and vasculitis (including glomerulonephritis), acute and chronic rejection of transplanted organs, graft versus host disease (GVHF), ischaemic/reperfusion damage of organs following surgical intervention, vasculopathy of venous bypasses, (pre)eclampsia and/or pregnancy-induced hypertension, arterial hypertension and its consequential diseases (left cardiac hypertrophy, formation of aneurysms with the risk of mass haemorrhages and vascular wall transformation of arteries and arterioles), pulmonary hypertension, chronic renal insufficiency, chronic obstructive pulmonary disease (COPD), bacterial infections and their consequential diseases (e.g. *helicobacter pylori* gastritis, tubercular pericarditis, Lyme-borreliosis with subsequent *borrelia* arthritis and/or neuroborreliosis), post-infection complications of infections with cytomegaly, hepatitis B and C, herpes and HI (human immunodeficiency) viruses, such as portal hypertension and fibrosis and/or opportunistic infections, especially *pneumocystis-carnii*-pneumonia.

Apart from the essential condition, that the decoy oligonucleotides according to the invention neutralise the inhibitory transcription factor effectively in vitro, it is critical for therapeutic efficacy, that the DNA molecule is absorbed into the target cell rapidly and to an adequate extent. Moreover, the cis-element decoy according to the invention should not exceed a given length, because this is limiting for the transport into the target cell. Any decoy oligonucleotide with a length of at least 10 bp (consensus core-binding sequence) up to a length of approximately 30 bp, preferably up to a length of approximately 27 base pairs, by particular preference up to a length of approximately 23, by particular preference with a length of 9, 10, 11, 12, 13, 14, 15, 16, 17, 18, 19, 20, 21, 22 or 23 base pairs, is suitable.

Since the cis-element decoy is a double-strand nucleic acid, each decoy oligonucleotide includes not only the sense or forward sequence but also the complementary antisense or reverse sequence. Preferred decoy oligonucleotides according to the invention provide a 10-mer core-binding sequence for the inhibitory transcription factor, as contained in SEQ ID NO: 33. The cis-element decoy can, however, also provide a sequence different from the above sequence and can be longer than a 10-mer. The sequences as contained in SEQ ID NO: 1 to SEQ ID NO: 34 are particularly preferred. This listing of preferred sequences is not finite. It is evident to a person skilled in the art that a plurality of sequences can be used as inhibitors for the transcription factor, so long as they provide the conditions of the 10-mer consensus core-binding sequence listed above and have an affinity to the transcription factor.

The affinity of the binding of a nucleic acid sequence to this transcription factor can be measured by the use of the Electrophoretic Mobility Shift Assay (EMSA) (Sambrook et al. (1989), Molecular Cloning, Cold Spring, Harbor Laboratory Press; Krzesz et al. (1999) FEBS Lett, 453, 191). This test system is suitable for quality control of nucleic acids, which are intended for use in the method of the present invention, or for the measurement of the optimum length of a binding position. It is also suitable for the identification of other sequences which are bound by the transcription factor.

The method of the present invention modulates the transcription of a gene or of genes in such a manner that the gene or genes, e.g. eNOS, are expressed to an increased extent. Increased expression within the framework of the present invention means that the transcription rate is increased by comparison with cells, which are not treated with a decoy oligonucleotide according to be invention. An increase of this kind can be measured, for example, by Northern blot (Sambrook et al., 1989) or RT-PCR (Sambrook et al., 1989). An increase of this kind is typically at least a 2-fold, especially at least a 5-fold, in particular at least a 10-fold inhibition of the gene expression.

Oligonucleotides are generally rapidly broken down by endonucleases and exonucleases, especially DNases and RNases in the cell. Accordingly the nucleic acids can be modified in order to stabilise them against degradation, so that a higher concentration of the oligonucleotides is maintained for a longer time in the cell. A stabilisation of this kind can typically be obtained by the insertion of one or more modified internucleotide bonds.

A successfully stabilised DNA oligonucleotide or decoy oligonucleotide does not necessarily contain a modification at each internucleotide bond. The internucleotide bonds are preferably modified at the relevant ends of both oligonucleotides of the cis-element decoy. In this context, the last six, five, four, three, two or the last, or one or more internucleotide bonds within the last six internucleotide bonds, can be modified.

Furthermore, various modifications of the internucleotide bonds can be inserted into the nucleic acid, and the resulting decoy oligonucleotide can be tested for sequence-specific binding to the inhibitory transcription factor using the routine EMSA test system. This test system allows the measurement of the binding constant of the cis-element decoy and accordingly a measure of whether the affinity has been changed by the modification. Modified cis-element decoys, which still show an adequate binding, can be selected, wherein an adequate binding is understood as at least approximately 50% or at least approximately 75%, and by particular preference approximately 100% of the binding of the unmodified nucleic acid.

Cis-element decoys with modified internucleotide bonds, which still show adequate binding, can be tested to determine whether they are more stable in the cell than unmodified cis-element decoys. The cells "transfected" with the cis-element decoys according to the invention are investigated at different times for the quantity of the cis-element decoy still present. In this context, a cis-element decoy marked with a fluorescence dye (e.g. Texas Red) or a radioactively marked (e.g. $^{35}$S) cis-element is used by preference, with subsequent digital fluorescence microscopy or autoradiography or scintigraphy. A successfully modified cis-element decoy has a half-life in the cell, which is greater than an unmodified cis-element decoy, preferably at least 48 hours, by greater preference at least approximately 4 days, by greatest preference at least 7 days.

Suitable modified internucleotide bonds are summarised in Uhlmann and Peyman, ((1990) Chem. Rev. 90, 544). Modified internucleotide phosphate residues and/or non-phosphorus bridges in a nucleic acid, which can be used in a method according to the present invention contain, for example, methyl phosphonate, phosphorothioate, phosphorodithioate, phosphoramidate, phosphate ester, while non-phosphorus-internucleotide analogues contain, for example, siloxane bridges, carbonate bridges, carboxymethyl ester bridges, acetamide bridges and/or thioether bridges. When using phosphorothioate-modified internucleotide bonds, these should preferably not be disposed between the bases Cytosine and Guanine, because this can lead to an activation of the target cells of the cis-element decoy in the form of an inflammatory reaction.

Another embodiment of the invention is the stabilisation of nucleic acids by the insertion of structural features into the nucleic acids, which increase the half-life of the nucleic acids. Such structures, which contain hairpin and dumbell DNA, are disclosed in U.S. Pat. No. 5,683,985. At the same time, modified internucleotide phosphate residues and/or non-phosphorus bridges can be introduced together with the named structures. The resulting nucleic acids can be tested for binding and stability in the test system described above.

A cis-element decoy of the present invention is rapidly absorbed into the cell. An adequate absorption is characterised by the modulation of the expression of one or more genes, which are subject to a control by the target transcription factor (e.g. eNOS). The cis-element decoy of the present invention modulates the transcription of a gene or genes in a preferred manner after approximately 4 hours of contact with the cell, by greater preference after 2 hours, after approximately 1 hour, after approximately 30 minutes and by the greatest preference after approximately 10 minutes. A typical mixture, which is used in an experiment of this kind contains 10 µmol/l cis-element decoy.

In order to ensure the efficacy of the therapeutic decoy oligonucleotides, it is desirable to investigate and/or diagnose the patients for the $^{-786}$C/T-variance, that is, to determine whether they are heterozygotic or homozygotic carriers of the $^{-786}$C-variant of the eNOS gene, before application of the decoy oligonucleotides, wherein the diagnosis method according to the invention, which preferably includes a real-time-PCR and subsequent melting curve analysis or a restriction fragment length polymorphism analysis (RFLP-analysis) is used.

Furthermore, it is desirable to use the diagnosis method according to the invention with patients, who must undergo a surgical intervention, in which, for example, the blood supply to one or more organs is temporarily interrupted or one or more autologous vascular transplants are transferred (e.g. aorto-coronary venous bypass surgery), in order to implement a treatment with the decoy oligonucleotides according to the invention and/or with drugs, which increase the NO-synthesis capacity of the vascular endothelium, such as angiotensin-conversion enzyme (ACE)-inhibitors, HMG-CoA-reductase inhibitors, antioxidants or nitric oxide-releasing vasodilators, during or following the surgical intervention. Furthermore, genotyping with the diagnosis method according to the invention should also be carried out in the case of organ donors, in order to treat the transplant between explantation and implantation (i.e. ex vivo) and/or to treat the organ recipient for a period of at least 3 days, by greater preference at least approximately 2 weeks, by greatest preference at least approximately 6 months, with the decoy oligonucleotides according to the invention and/or with the drugs named above.

Furthermore, the diagnosis methods according to the invention can be used to evaluate the individual risk to a person, of suffering from one of the diseases associated with the $^{-786}$C/T-variance of the eNOS gene and to advise the carriers of the $^{-786}$C/C genotype by way of a preventive strategy, especially with regard to the reduction of further risk factors.

Moreover, the diagnosis methods according to the invention can be used to provide carriers of the $^{-786}$C/C-genotype—as an alternative to or in addition to the treatment with the decoy oligonucleotides according to the invention—with a treatment with drugs, which increase the NO-synthesis capacity of the vascular endothelium and/or which increase the bioavailability of nitric oxide in the organism, such as angiotensin-conversion enzyme (ACE)-inhibitors, HMG-CoA-reductase-inhibitors, antioxidants or nitric oxide-releasing vasodilators.

The present invention therefore relates to methods for the diagnosis of a $^{-786}$C/T-variance in the human eNOS-gene, comprising the stages: addition of DNA oligonucleotides to a patient-DNA-sample, wherein a DNA oligonucleotide provides a sequence, which is disposed upstream of the –786 position of the eNOS-gene and corresponds to the sense strand, and another DNA oligonucleotide provides a sequence, which is disposed downstream of the –786 position of the eNOS-gene and corresponds to the antisense strand; implementation of a polymerase-chain reaction (PCR); implementation of DNA splitting with a restriction enzyme, which provides a recognition sequence, which is at least 4 nucleotides long and contains the sequence 5'-CCGG-3' but not the sequence 5'-CTGG-3'; and demonstration of the DNA fragments obtained by the DNA splitting. The DNA oligonucleotides act as primers for the PCR.

The term eNOS sequence refers to the sequence listed under the GenBank Accession Number L10693 (gi:348219), which is also referred to in the present document as the sense strand and corresponds to the strand which contains the mRNA sequence of the eNOS-gene product. The start is marked with +1; and accordingly, the position –786 is disposed upstream, before the start point. The strand complementary to the sense strand is referred to as the antisense strand, which is also known as the template.

The DNA oligonucleotides (primers) can be of any length required for a PCR. Furthermore, the DNA oligonucleotides can provide such sequences from the eNOS-gene or the 5'-region of the eNOS-gene, which allow the implementation of a PCR. For this purpose, the primers must be sufficiently far apart so that a detection of the amplificates and the split amplificates is possible, but not so far that no further amplificate can be produced. Moreover, the primers should be selected in such a manner that, in the case of a DNA splitting, DNA fragments are formed with a sufficiently different size to allow them to be readily demonstrated. The primers preferably have the sequences according to SEQ ID NO: 35 and 36. The restriction enzyme is preferably HpaII, and the detection method is an agarose-gel-electrophoresis or a capillary electrophoresis.

Moreover, the present invention relates to a kit for the implementation of the method according to the invention, comprising the above DNA oligonucleotides (primers), reagents for the implementation of a PCR, preferably including the Taq polymerase, a restriction enzyme and reagents for the implementation of DNA splitting.

Furthermore, the present invention relates to a method for rapid determination of the $^{-786}$C/T-variance of the human eNOS-gene, comprising the following stages: addition of DNA oligonucleotides to a patient DNA-sample, wherein one DNA oligonucleotide provides a sequence, which is disposed upstream of the −786 position of the eNOS-gene and corresponds to the sense strand (primer 1), a further fluorescence-dye-modified DNA oligonucleotide provides a sequence, which includes the −786 position of the eNOS-gene and corresponds to the sense or antisense strand and is complementary to the $^{-786}$C-variant of the eNOS-gene promoter (detection probe), another fluorescence-dye-modified DNA oligonucleotide provides a sequence, which corresponds to the sense or antisense strand (anchor probe), wherein the 3′-end of the anchor probe is disposed 1-5 nucleotides upstream of the 5′-end of the detection probe, if the anchor and detection probe respectively correspond to the sense strand, and wherein the 5′-end of the anchor probe is disposed 1-5 nucleotides upstream of the 3′-end of the detection probe, if the anchor and detection probe respectively correspond to the antisense strand, and another DNA oligonucleotide provides a sequence, which is disposed downstream of the −786 position of the eNOS-gene and corresponds to the antisense strand (primer 2); implementation of a polymerase-chain reaction (PCR); and demonstration of the $^{-786}$C and/or $^{-786}$T-variants by means of a fluorescence-resonance energy transfer (FRET)-supported DNA-melting curve analysis (FIG. 7).

The primers 1 and 2 can have any length required for a PCR. Furthermore, the primers can provide such sequences from the eNOS-gene or the 5′-region of the eNOS-gene, which allow the implementation of a PCR. For this purpose, the primers must be sufficiently far apart, to allow a demonstration of the amplificates and optionally of the split amplificates, but not so far that no further amplificate can be produced. By preference, primer 1 has the sequence 5′-CTGGGAACTGTAGTTTCCCTAG-3′ according to SEQ ID NO: 56, and primer 2 has the sequence 5′-ACCCTGTCAT-TCAGTGACGCAC-3′ according to SEQ ID NO: 57.

The anchor probe and also the detection probe used in the method are, by preference, both complementary to the sense strand and provide the sequence according to SEQ ID NO: 37 (5′-GGGTCAGCCGGCCAGGGAA-3′) for the detection probe and the sequence according to SEQ ID NO: 38 (5′-AGCTTGATGCCCTGGTGGGAG-3′) for the anchor probe. The detection probe is coupled covalently at the 3′-end to a fluorescence dye (e.g. fluorescein, excitation wavelength 494 nm). The anchor probe is coupled covalently at the 5′-end to a fluorescence dye, which is different from that of the detection probe (e.g. LC Red-640, emission wavelength 640 nm). Furthermore, the anchor probe is phosphorylated at the 3′-position of the last desoxyribose, preferably with $PO_4^{3-}$. The anchor probe has a melting temperature of 5-10° C. above the melting point of the detection probe. The dye combination is selected in such a manner that the excited dye of the detection probe is suitable to excite the dye of the anchor probe efficiently by FRET to such an extent, that it emits light of a defined wavelength as long as both probes are in the immediate proximity of one another. The detection probe and also the anchor probe are not suitable for the PCR, because they do not allow an enzymatic chain extension as a result of their chemical modification in the 3′ or respectively 5′ position.

In a further preferred embodiment, the anchor probe and the detection probe used in the method are both complementary to the antisense strand and provide the sequence according to SEQ ID NO: 59 (5′-TTCCCTGGCCGGCTGA-3′) for the detection probe and the sequence according to SEQ ID NO: 58 (5′-GCTCCCACCAGGGCATCAAGCT-3′) for the anchor probe. The detection probe is coupled at the 5′-end covalently to a fluorescence dye (e.g. LC Red-640). The anchor probe (SEQ ID NO: 58) is coupled covalently at the 3′-end to a fluorescence dye, which differs from the detection probe (e.g. fluorescein). Furthermore, the detection probe is phosphorylated at 3′-position of the last desoxyribose, preferably with $PO_4^{3-}$. The anchor provides a melting temperature of 5-10° C. above the melting point of the detection probe. The dye combination is selected in such a manner that the excited dye of the anchor probe is suitable to excite the dye of the detection probe efficiently by FRET to such an extent that it emits light of a defined wavelength so long as both probes are in the immediate proximity of one another.

The anchor probe therefore preferably has a sequence according to SEQ ID NO: 38 or 58, and the detection probe preferably has a sequence according to SEQ ID NO: 37 for 59. It is evident to a person skilled in the art, that DNA oligonucleotides, for example, with other sequences than specifically listed here can be used as detection probes and/or anchor probes. Furthermore, the detection probes and anchor probes used in the method according to the invention need not necessarily bind the same strand but, for example, the detection probe can bind the sense strand and the anchor probe can bind the antisense strand or vice versa. In such a case, it is not necessary for the sequences of the probes to be selected so that the probes are positioned in immediate proximity.

For the determination of the $^{-786}$C/T-variance of the human eNOS-gene of a patient sample, the primers 1 and 2 described above and the detection probe and anchor probe are added to a PCR mixture alongside the reagents necessary for the PCR and the patient DNA to be investigated. After the PCR-amplification, mediated by the primers 1 and 2, of a fragment of the eNOS-promoter, which contains the position −786 of the gene, the temperature of the mixture is raised so that all the DNA double strands are denatured. Following this, the temperature is again reduced so that the detection and anchor probes hybridise with the sense and antisense strands of the amplified fragment respectively, in dependence upon whether the probe combination is complementary to the sense or antisense strand (see FIG. 8).

Now, for example, in the case of the probes according to SEQ ID NO: 37 and 38, which are complementary to the sense strand, the melting curve is recorded by excitation of the dye of the detection probe and continuous measurement of the fluorescence of the anchor probe at the same time as increasing the temperature (e.g. approximately 0.1° C. per second). In this context, the fact is exploited that the transfer of the excitation energy of the dye of the detection probe acts on that of the anchor probe only for as long as both probes are bound to the sense strand. The $^{-786}$T-variant is distinguished from the $^{-786}$C-variant via the temperature at which the detection probe melts away from the sense strand, and accordingly, the FRET-induced fluorescence is significantly reduced. For the detection probe, this occurs approximately 12° C. sooner with fragments of the $^{-786}$T-variant than in the case of sense strands of the $^{-786}$C-variant because of the occurrence of the G-T-mismatch.

Furthermore, in the case of the probes according to SEQ ID NO: 58 and 59, which are complementary to the antisense strand, the melting curve is recorded by excitation of the dye of the anchor probe and continuous measurement of the fluorescence of the detection probe at the same time as increasing the temperature (e.g. approximately 0.1° C. per second). In this context, the fact is exploited that the transfer of the excitation energy of the dye of the anchor probe acts on that of the detection probe only for as long as both probes are bound to the antisense strand. The $^{-786}$T-variant is distinguished from the $^{-786}$C-variant via the temperature, at which the detection probe melts away from the antisense strand, and accordingly, the FRET-induced fluorescence is significantly reduced. For the detection probe, this occurs approximately 12° C. sooner in the case of fragments of the $^{-786}$variant than in the case of antisense strands of the $^{-786}$C-variant because of the occurrence of the C-A-mismatch.

For the detection, a fluorescence-based real-time PCR device (e.g. the LightCycler manufactured by Roche) is preferably used. It is evident to a person skilled in the art, that not only one genotype can be determined a in a PCR, but more than one genotype can be measured in a PCR, using a so-called multiplex-PCR.

Furthermore, the present invention relates to DNA oligonucleotides with the sequence according to SEQ ID NO: 35 to 38 and 56 to 59.

Moreover, the present invention relates to a kit for the implementation of the method according to the invention, comprising the primers 1 and 2 mentioned above, two further DNA oligonucleotides (detection probe and anchor probe), reagents for the implementation of a PCR preferably including the Taq polymerase, and reagents for the implementation of a melting curve analysis.

The present invention also relates to a method for modulating the transcription of at least one gene in cells, especially in eNOS-expressing cells, such as endothelial cells, epithelial cell of the lungs, kidneys and the female urogenital tract, myocardial cells, thrombocytes and neuronal cells (hippocampus), wherein the method comprises the stage of contacting the named cells with a mixture containing one or more decoy oligonucleotides according to the invention, which are capable of binding in a sequence-specific manner to the inhibitory transcription factor. One preferred method is, for example, the intra-articular injection of the nucleic acid-containing mixture into one or more joints in patients with rheumatoid arthritis.

The mixture containing the cis-element decoys according to the invention is brought into contact with the target cells (e.g. endothelial cells). The goal of this bringing-into-contact is the transfer of the cis-element decoys, which bind the inhibitory transcription factor, into the target cell (that is, for example, the eNOS-expressing endothelial cell). Accordingly, nucleic acid modification and/or additives or excipients, which are known to increase the penetration of membranes, can be used within the framework of the present invention (Uhlmann and Peyman (1990) Chem. Rev, 90, 544).

In one preferred embodiment, a mixture according to the invention brought into contact with the target cells contains essentially only nucleic acid and buffers. The concentration range appropriate for the decoy oligonucleotides is approximately 0.1 to 100 µmol/l, preferably approximately 0.5 to 25 µmol/l and by particular preference approximately 10 µmol. One or more appropriate buffers can be added. An example of a buffer of this kind is a modified Ringer's solution containing 145 mmol/l Na$^+$, 5 mmol/l K$^+$, 11 mmol/l Cl$^-$, 2 mmol/l Ca$^{2+}$, 1 mmol/l Mg$^{2+}$, 10 mmol/l Hepes, 145 mmol/l Isethionate, 10 mmol/l D-glucose, pH 6.5.

In a further embodiment of the invention, the mixture additionally contains at least one additive and/or excipient. Additives and/or excipients such as lipids, cationic lipids, polymers, liposomes, nanoparticles, nucleic acid aptamers, peptides and proteins, which are bound to DNA, or synthetic peptide-DNA-molecules are intended, for example, to increase the introduction of nucleic acids into the cell, in order to direct the mixture to only one subgroup of cells, to prevent the breakdown of the nucleic acid in the cell and to assist the storage of the nucleic acid mixture before use. Examples of peptides and proteins or synthetic peptide DNA molecules are, for example, antibodies, antibody fragments, ligands, adhesion molecules, all of which can be modified or unmodified.

Additives, which stabilise the cis-element decoys in the cell, are, for example, nucleic acid-condensing substances such as cationic polymers, poly-L-lysine or polyethylenimine.

The mixture used in the method of the present invention is preferably applied locally by injection, infusion, catheter, pluronic gels, polymers which release medicines gradually or any other device, which allows local access. The ex vivo application of the mixture (infusion and/or incubation), used in the method of the present invention, also allows a local access.

The following examples are provided only by way of explanation and in no sense restrict the scope of the invention.

1. Patients

To analyse the frequency distribution of the $^{-786}$C/T-variance of the eNOS-gene in coronary heart disease (CHD), rheumatoid arthritis, multiple sclerosis or Crohn's disease, genomic DNA was isolated from patients' blood samples (approximately 2 ml), and this was investigated for the variance by means of PCR amplification and subsequent FRLP-analysis (see below).

In the analysis of patients with rheumatoid arthritis, it was possible to draw on two already-existing patient groups. In this context, anonymous (numerical code) DNA samples from male and female patients from the Rheumatology Department of the University of Göttingen and the Department of Rheumatology at the University Hospital Freiburg were tested for the variance. Both patient groups offer a typical distribution of male and female patients with rheumatoid arthritis, that is to say, 80% of the affected persons are female. The age profile extended from 20 years to 80 years with peaks in patient numbers at 35-40 years (early onset) and 60-70 years (late onset).

To analyse the $^{-786}$C/T-variance of the eNOS-gene in cases of coronary heart disease, blood samples were taken during the implementation of a cardiac catheter investigation. In this manner, it was possible to establish or exclude the presence of the disease unambiguously. Verbal and written explanations were given to all patients before taking the blood test and all patients had given their written consent for the use of the blood samples. The genotyping took place in anonymous form (numerical coding); age, diagnosis, sex and risk-factor profile of the associated persons were disclosed after the completion of the analysis. Individuals up to 64 years were used for the statistical analysis of the genotype distribution. The distribution of the already-known primary risk factors for CHD (hypertension, diabetes, cigarette smoking and hypercholesterolaemia) was independent of the genotype of the relevant patient.

TABLE 1

$^{-786}$C/T-polymorphism of the eNOS-gene in patients with coronary heart disease, OR, odds ratio, by comparison with control group. Control group, DNA from umbilical cord.

|  | C/C | C/T | T/T | Total |
| --- | --- | --- | --- | --- |
| Patients with CHD | 33 | 89 | 52 | 174 |
| OR 1.81 | (19.0%) | (51.1%) | (29.9%) |  |
| Patients without CHD | 7 | 69 | 82 | 158 |
| OR 0.35 | (4.4%) | (43.7%) | (51.9%) |  |
| Control group | 78 | 319 | 265 | 662 |
|  | (11.8%) | (48.2%) | (40.0%) |  |

To provide a control group for the genotype distribution, DNA from the umbilical artery from neonates from Göttingen and surroundings (within a radius of approximately 70 km) was used. These samples were also anonymous, and the parents of the children had previously signed a declaration of consent for the appropriate use of the umbilical cord. For the genotyping of patients with multiple sclerosis or Crohn's disease, anonymous genomic DNA samples were available (University Hospital Charité Berlin, Institute for Neuroimmunology and University of Göttingen, Department of Immunology).

TABLE 2

$^{-786}$C/T-polymorphism of the eNOS-gene in patients with rheumatoid arthritis and Crohn's disease, OR, odds ratio, by comparison with control group. Control group, DNA from umbilical cord.

|  | C/C | C/T | T/T | Total |
|---|---|---|---|---|
| Patients with rheumatoid arthritis | 99 | 262 | 223 | 584 |
| OR 1.55 | (17.0%) | (44.9%) | (38.1%) |  |
| Patients with Crohn's disease | 18 | 52 | 40 | 110 |
| OR 0.47 | (16.4%) | (47.3%) | (36.4%) |  |
| Control group | 78 | 319 | 265 | 662 |
|  | (11.8%) | (48.2%) | (40.0%) |  |

2. Genotyping

By comparison with the $^{-786}$T-variant, the $^{-786}$C-variant of the human eNOS-gene promoter has one additional restriction interface for the restriction enzyme Hpa II and is therefore accessible to a classical restriction fragment length polymorphism analysis (RFLP-analysis). Alternatively, the above-named variance is also accessible to a real-time-PCR followed by a FRET-analysis.

RFLP-Analysis

In the RFLP-analysis, from genomic DNA (from blood obtained using the QIAamp DNA Mini-Kit manufactured by Qiagen, Hilden) with the assistance of eNOS-promoter-specific primer (forward primer 5'-GAGTCTGGCCAACA-CAAATCC-3' (SEQ ID NO: 35); reverse primer 5'-GAC-CTCTAGGGTCATGCAGGT-3') (SEQ ID NO: 36) by polymerase chain reaction (PCR), a DNA fragment (657 base pairs (bp) from position −1135 to −456 of the human eNOS-gene was amplified and then subjected to a specific hydrolysis using the restriction endonuclease Hpa II. The resulting DNA fragments were analysed by means of agarose gel-electrophoresis. Depending on the genotype, 2 or 3 smaller DNA fragments are produced from the 657 bp fragment. While the T-variant of the promoter in the segment observed has only one Hpa II interface and accordingly breaks down after hydrolysis by Hpa II into two fragments (284 bp and 373 bp), the additional interface of the C-variant causes the formation of 3 fragments (46 bp—not detectable with the electrophoresis system used—284 bp and 327 bp). To this extent, the three possible genotypes ($^{-786}$C/C, $^{-786}$T/T and $^{-786}$C/T) could be identified unambiguously after electrophoresis on the basis of the following fragment pattern: $^{-786}$T/T: 284 and 373 bp; $^{-786}$C/C: 284 and 327 bp; and $^{-786}$C/T: 284, 327 and 373 bp.

FRET-Analysis

In the FRET analysis, from genomic DNA (from blood obtained using the QIAamp DNA Mini-Kit manufactured by Qiagen, Hilden) with the assistance of eNOS-promoter-specific primer (forward primer 5'-CTGGGAACTGTAGTTTC-CCTAG-3' (SEQ ID NO: 56); reverse primer 5'-ACCCTGT-CATTCAGTGACGCAC-3') (SEQ ID NO: 57) by polymerase chain reaction (PCR) in a real-time PCR device (LightCycler manufactured by Roche), a DNA fragment (137 bp) from position −848 to −711 of the human eNOS-gene, GenBank Accession No L10693) was amplified. After the PCR-amplification, using the anchor probe (SEQ ID NO: 58) and detection probe (SEQ ID NO: 59) added before the PCR, a melting curve was registered, which recorded the fluorescence resonance energy transfer from the fluorescence dye of the anchor probe (fluorescein) to that of the detection probe (LC-Red 640). On the basis of their melting point (approximately 48° C.), T-alleles were unambiguously distinguished from C-alleles (melting point approximately 60° C.).

3. Cell Culture

Human endothelial cells from umbilical veins were isolated from previously genotyped donors by treatment with 1.6 U/ml Dispase in Hepes-modified Tyrode solution for 30 minutes at 37° C. and cultivated on gelatine-coated-6-well tissue culture dishes (2 mg/ml gelatine in 0.1 M HCl for 30 minutes at room temperature) in 1.5 ml M199 Medium (Gibco Life Technologies, Karlruhe, Germany), containing 20% foetal calf serum, 50 U/ml penicillin, 50 µg/ml streptomycin, 10 U/ml nystatin, 5 mmol/l HEPES and 5 mmol/l TES, 1 µg/ml heparin and 40 µg/ml endothelial growth factor. They were identified by their typical pavement morphology; positive immuno-staining for von Willebrandt-Factor (vWF) and fluorimetric detection (FACS) of PCAM-1 (CD31) and negative immuno-staining for smooth muscular α-actin (Krzesz et al. (1999), FEBS Lett. 453, 191).

The mouse myeloma cell line P3xTBA7 (stable transfected with human CD40 ligands) and P3x63Ag8.653 (non-transfected control cells) were cultivated in RPMA 1640 Medium (Life Technologies), containing 10% foetal calf serum, 50 U/ml penicillin, 50 µg/ml streptomycin and 10 U/ml nystatin. In the case of the cultivated endothelial cells, wall shear stress (generally 30 dyn/cm$^2$ for 24 to 36 hours), was applied using a cone/plate viscometer capable of being placed in the cultivation cabinet, as described in Schubert et al. (2000), Circ. Res. 87, 1188, except for the dimensions of the culture dishes (3.5 cm by contrast with 10.0 cm diameter).

4. RT-PCR-Analysis

Conventional RT-PCR

The cellular total RNA was isolated using the Qiagen RNeasy Kit (Qiagen, Hilden, Germany), following this, a cDNA-synthesis was implemented with 1-5 µg RNA and 200 U Superscript™ II Reverser Transcriptase (Life Technologies) in a total volume of 20 µl in accordance with the manufacturer's instructions. To calibrate the cDNA quantities in the various samples, 5 µl of the 1:10 diluted cDNA solution (corresponding to an RNA equivalent of 25-125 ng) were subjected to a PCR reaction (1 U Taq DNA polymerase ([Life Technologies]) with specific primers for the constitutively expressed gene products glycerine aldehyde phosphate dehydrogenase (GAPDH) and ribosomal protein L32 (rpl32). In this context, GAPDH and rpl32 were used as internal calibration standards. The PCR products were separated on 1.5% agarose gels containing 0.1% ethidium bromide, and the intensity of the bands was measured densiometrically with a CCD camera system and the One-Dscan gel analysis manufactured by Scanalytics (Billerica, Mass., USA), in order to adapt the volumes of the cDNA in subsequent PCR-analyses.

All PCR-reactions were carried out individually for each primer pair in a licensed Thermocycler (PC-Personal Cycler, Biometra, Göttingen). The individual PCR-conditions were as follows: eNOS—product size 581 bp, 30 cycles, deposition temperature 58° C., forward primer 5'-GGAACCTGTGT-GACCCTC-3' (SEQ ID NO: 39), reverse primer 5'-CCACGTCATACTCATCCA-3' (SEQ ID NO: 40) IL-12p40—281 bp, 30 cycles, 62° C., 5'-GTACTCCACAT-TCCTACTTCT-3' (SEQ ID NO: 41), 5'-TTTGGGTCTAT-TCCGTTGTGTC-3' (SEQ ID NO: 42) IL-10 receptor—565 bp, 32 cycles, 59° C., 5'-GGACACCCATCCCAAAT-CAGTC-3' (SEQ ID NO: 43), 5'-CACGGTGAAATACTGC-CTGGTG-3' (SEQ ID NO: 44) GAPDH—571 bp, 19 cycles, 58° C., 5'-TCACCATCTTCCAGGAGCG-3' (SEQ ID NO: 45), 5'-CTGCTTCACCACCTTCTTGA-3' (SEQ ID NO: 46) rpl32—368 bp, 20 cycles, 60° C., 5'-GTTCATCCGGCAC-CAGTCAG-3' (SEQ ID NO: 47), 5'-ACGTGCACAT-GAGCTGCCTAC-3' (SEQ ID NO: 48)

All of the amplificates were unambiguously identified by DNA sequencing (ABI PRISM 3100 Genetic Analyzer, Pharmacia, Freiburg, Germany) with subsequent calibration with the corresponding gene sequences (Reference: GenBank, NCBI, Bethesda, USA)

Real-Time-PCR

The real-time-PCR demonstration of the eNOS mRNA expression was implemented essentially as described by Wagner et al. (2003), J. Immunol. 170, 1462. Five μl cDNA (M-MLV Reverse Transcriptase; Promega, Mannheim, Germany) corresponding to 10 ng total RNA were used for each PCR reaction, which was implemented using the QuantiTect SYBR Green PCR-Kits manufactured by Qiagen (Hilden, Germany) and a LightCycler (Roche Diagnostics, Mannheim, Germany). The eNOS-specific mRNA fragments (GenBank Accession No. NM 000603, 129 bp, position 1151 to 1279) were amplified using the forward primer 5'-GGAT-GTGGCTGTCTGCATGGAC-3' (SEQ ID NO: 60) and the reverse primer 5'-TGGTCCACGATGGTGACTTTGG-3' (SEQ ID NO: 61). For the purpose of normalisation, the cDNA for GAPDH (GenBank Accession No. BT006893, 138 bp. position 525 to 662) was amplified in parallel (forward primer 5'-GACCACAGTCCATGCCATCACTGC-3' (SEQ ID NO: 62); reverse primer 5'ATGACCTTGCCCACAGC-CTTGG-3' (SEQ ID NO: 63)). The procedure for amplification of the two genetic products consisted of a 15-minute long incubation at 95° C., followed by 40 cycles of 5 s at 95° C., 25 s at 58° C. and 10 s at 72° C. The melting curve was programmed with a gradient from 0.2° C./s from 65 to 95° C., and the fluorescence intensity after each cycle was measured. For the quantitative analysis, a standard curve for both genetic products was measured with serial dilutions of the corresponding PCR-fragments ($10^2$ to $5 \times 10^8$ copies/reaction). For this purpose, the genetic products were cloned in the plasmid pCR-TOPO (Invitrogen, Karlruhe, Germany).

5. Decoy Oligonucleotide Technique

Double-strand decoy oligonucleotides were manufactured from the complementary single-strand phosphorothioate-coupled oligonucleotides (Eurogentec, Köln, Germany) as described in Krzesz et al. (1999), FEBS Lett. 453, 191. The cultivated human endothelial cells were subjected to preliminary treatment for 4 hours with the relevant decoy oligonucleotides in a concentration of 10 μmol/l, and after the change of medium, added to the incubation medium in the same concentration. The single-strand sequences of the oligonucleotides were as follows (underlined letters denote phosphorothioate-coupled bases):

STAT-3           5'-CCTGCATTCTGGGAACTGTAG-3',     (SEQ ID NO: 49)

STAT-3 mutated   5'-CCTGTATGCCGTGAGCTATAG-3',     (SEQ ID NO: 50)

and the decoy oligonucleotides shown in Table 3 for the neutralisation of the transcription factors binding to the −786 position of the eNOS-gene. The sequence of the STAT-3 decoy oligonucleotides corresponds to the position −858 to −838 in the human eNOS-gene.

Table 3

Restoration of the inhibitory effect of IL-10 on the CD154-induced IL-12 p40 mRNA-expression (expressed as a percentage of the IL-12 p40 RNA expression in CD154-stimulated control cells; mean value S.E. of n individual experiments) in human cultivated endothelial cells from donors with $^{-786}$C/C-genotype by various cis-element decoys (in each case, only one strand of the decoy oligonucleotide is indicated together with the corresponding position in the promoter of the human eNOS-gene). The reference parameter is CD154-induced IL-12p40 mRNA expression after the addition of IL-10 in endothelial cells with $^{-786}$T/T-genotype (55±2% of the control, n+6; complete restoration) or respectively $^{-786}$C/C-genotype (136±16% of the control, n=21; no effect).

| SEQ ID NO | Position | Sequence (5'→3') | IL-12 p40 n (%) | |
|---|---|---|---|---|
| 1 | −800/−779 | AGCTCTTCCCTGGCCGGCTGAC | 32 ± 8 | 7 |
| 3 | −800/−779/T | AGCTCTTCCCTGGCTGGCTGAC | 60 ± 10 | 7 |
| 5 | −796/−774 | CTTCCCTGGCCGGCTGACCCTGC | 48 ± 7 | 5 |
| 7 | −796/−774/T | CTTCCCTGGCTGGCTGACCCTGC | 67 | 2 |
| 9 | −799/−781 | GCTCTTCCCTGGCCGGCTG | 65 | 2 |
| 1 | −802/−784 | CAAGCTCTTCCCTGGCCGG | 83 | 2 |
| 13 | −197/−779 | TCTTCCCTGGCCGGCTGAC | 41 ± 7 | 5 |
| 15 | −791/−773 | CTGGCCGGCTGACCCTGCC | 65 | 2 |
| 17 | −794/−779 | TCCCTGGCCGGCTGAC | 30 | 2 |
| 19 | −791/−782 | CTGGCCGGCT | 13 ± 9 | 3 |

-continued

| SEQ ID NO | Position | Sequence (5'→3') | IL-12 p40 n (%) | |
|---|---|---|---|---|
| 21 | -791/-782/T | CTGGCTGGCT | 47 ± 20 | 3 |
| 51 | -788/-770 | GCCGGCTGACCCTGCCTCA | 105 | 1 |
| 52 | artificial/T | TCTTCCCTAGCTGACTGAC | 136 ± 25 | 5 |
| 53 | artificial | TCCCTGACCGACTCAG | 80 ± 21 | 3 |
| 54 | artificial/T | TCCCTAGCTGACTGAC | 90 | 1 |

6. Electrophoretic Mobility Shift Analysis (EMSA)

The nuclear extracts and [$^{32}$P]-marked double-strand consensus oligonucleotides (Santa Cruz Biotechnologie, Heidelberg, Germany), non-denatured polyacrylamide gel electrophoresis, autoradiography and supershift analyses were implemented as described in Krzesz et al. (1999), FEBS Lett. 453, 191. In this context, the following decoy oligonucleotides (single-strand sequence, core-binding sequence is underlined) were used:

```
                                        (SEQ ID NO: 49)
    STAT-3   5'-CCTGCATTCTGGGAACTGTAG-3'

(SEQ ID NO: 55)
    SIE      5'-GTGCATTTCCCGTAAATCTTGTCTACA-3'
```

Both STAT-1 and STAT-3 bind to the oligonucleotides SIE. In this context, supershift analyses were additionally carried out with a monoclonal mouse-anti-human supershift antibody (Santa Cruz Biotechnologie) (addition in a concentration of 10 μg/ml to the nuclear extract for 1 hour at room temperature).

7. Western-Blot Analysis

The human umbilical cord endothelial cells were opened by freezing five times successively in liquid nitrogen and thawing at 37° C. Protein extracts were manufactured as described by Hecker et al. (1994) Biochem. J. 299, 247. 20-30 μg protein were separated using a 10% polyacrylamide gel electrophoresis under denaturing conditions in the presence of SDS according to a standard protocol and transferred to a BioTrace™ polyvinylidene fluoride transfer membrane (Pall Corporation, Rossdorf, Germany). For the immunological demonstration of the eNOS and the IL-10 receptor, monoclonal mouse-anti-human antibodies (BD Pharmingen, Heidelberg, Germany; 1:5000 or 1:3000 dilution) were used. The protein bands were detected after the addition of a peroxidase-coupled anti-mouse-IgG (1:3000, Sigma, Deisenhofen, Germany) using the Chemiluminescence method (SuperSignal Chemiluminescent Substrate, Pierce Chemical, Rockford, Ill., USA) and subsequent autoradiography (Hyperfilm™ MP, Amersham Pharmacia Biotech, Buckinghamshire, England). The application and transfer of identical protein quantities was shown after "stripping" of the transfer membrane (5 minutes 0.2 N NaOH, followed by 3×10 minutes washing with $H_2O$) by the demonstration of identical protein bands of β-actin with a monoclonal primary antibody and a peroxidase-coupled anti-mouse IgG (both manufactured by Sigma-Aldrich, 1:3000).

8. IL-12 p40 ELISA

The enzyme-coupled antibody binding assay (ELISA) is a standard method for quantitative analysis of proteins. It was used as described in Lienenlüke et al, (2000) Eur. J. Immunol. 30, 2864 for the demonstration of the IL-12 p40 sub-unit in the supernatant of the incubated human endothelial cells.

9. Statistical Analysis

Unless otherwise indicated, all data in the diagrams are shown as a mean value±SEM of n experiments. The statistical evaluation was implemented by means of one-sided variance analysis (ANOVA) followed by a Dunnett Post Test. A P-value of <0.05 was taken as a statistically significant difference.

The invention claimed is:

1. A double-stranded decoy oligonucleotide consisting of the nucleic acid sequence according to SEQ ID NO: 17 in one strand and SEQ ID NO:18 in the other strand.

2. The double-stranded decoy oligonucleotide according to claim 1, wherein said oligonucleotide is formulated as a pharmaceutical agent.

* * * * *